United States Patent
Maeta et al.

(10) Patent No.: US 12,116,419 B2
(45) Date of Patent: Oct. 15, 2024

(54) METHOD FOR IMPROVING AFFINITY OF ANTIBODY FOR ANTIGEN AND USE THEREOF

(71) Applicant: SYSMEX CORPORATION, Kobe (JP)

(72) Inventors: Shingo Maeta, Kobe (JP); Atsushi Fukunaga, Kobe (JP); Reema Bajaj, Kobe (JP)

(73) Assignee: SYSMEX CORPORATION, Kobe (JP)

(*) Notice: Subject to any disclaimer, the term of this patent is extended or adjusted under 35 U.S.C. 154(b) by 0 days.

(21) Appl. No.: 18/157,752

(22) Filed: Jan. 20, 2023

(65) Prior Publication Data

US 2023/0227578 A1    Jul. 20, 2023

Related U.S. Application Data

(63) Continuation of application No. 17/154,297, filed on Jan. 21, 2021, now Pat. No. 11,795,237.

(30) Foreign Application Priority Data

| Jan. 24, 2020 | (JP) | 2020-010411 |
| Jan. 24, 2020 | (JP) | 2020-010413 |
| Jan. 24, 2020 | (JP) | 2020-010414 |
| Jan. 24, 2020 | (JP) | 2020-010416 |
| Jan. 24, 2020 | (JP) | 2020-010417 |
| Jan. 24, 2020 | (JP) | 2020-010418 |
| Jan. 24, 2020 | (JP) | 2020-010419 |
| Jan. 24, 2020 | (JP) | 2020-010420 |
| May 28, 2020 | (JP) | 2020-093384 |
| May 28, 2020 | (JP) | 2020-093389 |
| May 28, 2020 | (JP) | 2020-093392 |
| May 28, 2020 | (JP) | 2020-093399 |
| May 28, 2020 | (JP) | 2020-093405 |
| May 28, 2020 | (JP) | 2020-093411 |
| May 28, 2020 | (JP) | 2020-093421 |
| May 28, 2020 | (JP) | 2020-093424 |

(51) Int. Cl.

| C07K 16/00 | (2006.01) |
| C07K 16/26 | (2006.01) |
| C07K 16/32 | (2006.01) |
| C07K 16/40 | (2006.01) |
| G16B 15/20 | (2019.01) |
| G16B 20/30 | (2019.01) |

(52) U.S. Cl.
CPC ............. C07K 16/40 (2013.01); C07K 16/00 (2013.01); C07K 16/26 (2013.01); C07K 16/32 (2013.01); G16B 15/20 (2019.02); G16B 20/30 (2019.02); C07K 2317/24 (2013.01); C07K 2317/51 (2013.01); C07K 2317/515 (2013.01); C07K 2317/54 (2013.01); C07K 2317/55 (2013.01); C07K 2317/567 (2013.01); C07K 2317/569 (2013.01); C07K 2317/622 (2013.01); C07K 2317/92 (2013.01)

(58) Field of Classification Search
CPC .................................. C07K 2317/567
See application file for complete search history.

(56) References Cited

U.S. PATENT DOCUMENTS

| 11,795,237 B2 * | 10/2023 | Maeta .............. C07K 16/26 |
| 2010/0098692 A1 | 4/2010 | Theuer et al. |
| 2011/0319597 A1 | 12/2011 | Simpson et al. |
| 2016/0168242 A1 | 6/2016 | Hass et al. |
| 2017/0247448 A1 | 8/2017 | Westerman |
| 2017/0247454 A1 | 8/2017 | Benz et al. |
| 2017/0320938 A1 | 11/2017 | Nicolau |
| 2018/0179298 A1 | 6/2018 | Maeta et al. |
| 2019/0144565 A1 | 5/2019 | Adams et al. |
| 2019/0345230 A1 | 11/2019 | Chen |
| 2019/0352389 A1 | 11/2019 | Seoane Suarez et al. |

FOREIGN PATENT DOCUMENTS

| WO | 2005/011376 A2 | 2/2005 |
| WO | 2013/084371 A1 | 6/2013 |

OTHER PUBLICATIONS

Chinese Office Action dated Aug. 25, 2023 in Application No. 202080069165.8.
Chinese Office Action dated Aug. 25, 2023 in Application No. 202110079131.3.
Chinese Office Action dated Aug. 25, 2023 in Application No. 202110087738.6.
Chinese Office Action issued Sep. 20, 2023 in Application No. 202110085059.5.
Office Action dated Jul. 29, 2023, issued in Chinese Application No. 202080070223.9.
Office Action dated Jul. 20, 2023, issued in Chinese Application No. 202110079250.9.
First Office Action issued Jul. 13, 2023, from the Chinese Patent Office in Chinese Application No. 202110080299.6.
Amita Datta-Mannan, et al., "Balancing charge in the complementarity-determining regions of humanized mAbs without affecting pI reduces non-specific binding and improves the pharmacokinetics", mAbs, 2015, pp. 483-493, vol. 7, Issue 3.
Annemarie Honegger, et al., "The Influence of the Buried Glutamine or Glutamate Residue in Position 6 on the Structure of Immunoglobulin Variable Domains", J. Mol. Biol., 2001, pp. 687-699, vol. 309.

(Continued)

*Primary Examiner* — Jeffrey E. Russel
(74) *Attorney, Agent, or Firm* — Sughrue Mion, PLLC

(57) ABSTRACT

Disclosed is a method for improving affinity of an antibody for an antigen, comprising, in an unmodified antibody, improving affinity for an antigen as compared to the unmodified antibody, by changing 18th, 20th and 22nd amino acid residues of a light chain defined by Kabat method to charged amino acid residues.

12 Claims, 10 Drawing Sheets

Specification includes a Sequence Listing.

(56) References Cited

OTHER PUBLICATIONS

Atsushi Fukunaga, "Study on improving the affinity of an antibody for its antigen via Long-range electrostatic interactions", Kyushu Univ Inst Repository, 2013, pp. 1-48.
Atsushi Fukunaga, et al., "Improving the affinity of an antibody for its antigen via long-range electrostatic interactions", Protein Engineering, Design & Selection, Nov. 7, 2013, pp. 1-8.
Bing Li, et al., "Framework selection can influence pharmacokinetics of a humanized therapeutic antibody through differences in molecule charge", mAbs, Oct. 2014, pp. 1255-1264, vol. 6, Issue 5.
Brian R. Miller, et al., Stability engineering of scFvs for the development of bispecific and multivalent antibodies, XP-002690428, Protein Engineering, Design & Selection, 2010, pp. 549-557, vol. 23, No. 7.
Communication dated Jul. 21, 2022 from the Taiwanese Patent Office in Taiwanese Application No. 109142632.
Communication dated Jun. 27, 2022 from the Taiwanese Patent Office in Taiwanese Application No. 109142631.
Extended European Search Report dated Jun. 21, 2021 from the European Patent Office in EP Application No. 21152854.2.
Extended European Search Report dated Jun. 21, 2021 from the European Patent Office in EP Application No. 21152856.7.
Extended European Search Report dated Jun. 21, 2021 from the European Patent Office in EP Application No. 21152857.5.
Extended European Search Report dated Jun. 21, 2021 from the European Patent Office in EP Application No. 21152859.1.
Extended European Search Report dated Jun. 21, 2021 from the European Patent Office in EP Application No. 21152860.9.
Extended European Search Report dated Jun. 21, 2021 from the European Patent Office in EP Application No. 21152861.7.
Fukunaga et al., "Improvement of antibody affinity by introduction of basic amino acid residues into the framework region", Biochemistry and Biophysics Reports, vol. 15 (2018) pp. 81-85 (5 pages total).
International Preliminary Report on Patentability with Written Opinion dated Jul. 26, 2022 in International Application No. PCT/JP2020/047491.
International Preliminary Report on Patentability with Written Opinion dated Jul. 26, 2022 in International Application No. PCT/JP2020/047498.
International Search Report dated Feb. 16, 2021 from the International Searching Authority in International Application No. PCT/JP2020/047491.
International Search Report dated Mar. 16, 2021 from the International Searching Authority in International Application No. PCT/JP2020/047498.
Kant et al., "Adaption of human antibody X and k light chain architectures to CDR repertoires", Protein Engineering, Design & Selection, 2019. vol. 32. No. 3, pp. 109-127 (19 pages total).
Margaret A. Holmes, et al., "Structural Effects of Framework Mutations on a Humanized Anti-Lysozyme Antibody1", XP-002366459, The Journal of Immunology, 2001, pp. 296-301.
Office Action dated Feb. 10, 2022 Issued by the Taiwanese Patent Office in Taiwanese Application No. 109142632.
Office Action dated Feb. 17, 2022 issued by the Taiwanese Patent Office in Taiwanese Application No. 109142631.
Shaun M. Lippow, et al., "Computational design of antibody-affinity improvement beyond in vivo maturation", Nature Biotechnology, XP-002615650, Oct. 2007, pp. 1171-1176, vol. 25, No. 10.
Veronica Quintero-Hernandez, et al., "The change of the scFv into the Fab format improves the stability and in vivo toxin neutralization capacity of recombinant antibodies", Molecular Immunology, 2007, pp. 1307-1315, vol. 44.
William R. Strohl, et al., "Therapeutic antibody engineering Current and future advances driving the strongest growth area in the pharmaceutical industry", Woodhead Publishing Series in Biomedicine: No. 11, pp. 124-127, (2012).
Written Opinion dated Feb. 16, 2021 from the International Searching Authority in International Application No. PCT/JP2020/047491.
Written Opinion dated Mar. 16, 2021 from the International Searching Authority in International Application No. PCT/JP2020/047498.
Non-Final Office Action dated Aug. 8, 2022 in U.S. Appl. No. 17/154,366.
Non-Final Office Action dated Sep. 21, 2022 issued in U.S. Appl. No. 17/154,340.
Chinese Office Action issued Aug. 16, 2023 in Application No. 202110085171.9.
Chinese Office Action dated Feb. 2, 2024 in Application No. 20210079250.9.
Office Action issued Feb. 20, 2024, in Taiwanese Application No. 109142632.
Extended European Search Report issued Feb. 23, 2024, in European Application No. 20915286.7.
Office Action issued Feb. 28, 2024, in Chinese Application No. 202110080299.6.
Office Action issued Mar. 23, 2024, in Chinese Application No. 202110085059.5.
Office Action issued Apr. 18, 2024, in Chinese Application No. 202080070223.9.
Shira Warszawski, et al., "Optimizing antibody affinity and stability by the automated design of the variable light-heavy chain interfaces", PLoS Computational Biology, Aug. 23, 2019, vol. 15, No. 8, pp. 1-24 (24 pages total).
Office Action issued Feb. 14, 2024, in U.S. Appl. No. 18/157,739.
Office Action issued Mar. 6, 2024, in U.S. Appl. No. 18/157,756.
Office Action issued Mar. 8, 2024, in U.S. Appl. No. 18/157,766.
Office Action issued Mar. 11, 2024, in U.S. Appl. No. 18/189,997.
Communication dated Jun. 15, 2024, issued in Chinese Application No. 202110087738.6.
Communication dated Jun. 19, 2024, issued in Chinese Application No. 202110085171.9.
Communication dated Jun. 20, 2024, issued in Chinese Application No. 202080069165.8.
Communication dated Jun. 22, 2024, issued in Chinese Application No. 202110079131.3.

* cited by examiner

| POSITION OF FR1 OF LIGHT CHAIN | L1 | L2 | L3 | L4 | L5 | L6 | L7 | L8 | L9 | L10 |
|---|---|---|---|---|---|---|---|---|---|---|
| TOTAL VALUE OF AMINO ACID FREQUENCIES (%) | 62.9 | 27.7 | 67.8 | 8.2 | 93.8 | 4.9 | 66.2 | 9.1 | 63.2 | 83.5 |
| RATIO OF SOLVENT-EXPOSED SURFACE AREA (%) | 69.0 | 7.1 | 88.1 | 0.0 | 84.8 | 0.0 | 100.0 | 54.8 | 111.5 | 74.0 |

| POSITION OF FR1 OF LIGHT CHAIN | L11 | L12 | L13 | L14 | L15 | L16 | L17 | L18 | L19 | L20 |
|---|---|---|---|---|---|---|---|---|---|---|
| TOTAL VALUE OF AMINO ACID FREQUENCIES (%) | 30.3 | 83.1 | 37.5 | 81.6 | 23.2 | 1.4 | 58.1 | 80.0 | 61.4 | 93.5 |
| RATIO OF SOLVENT-EXPOSED SURFACE AREA (%) | 26.8 | 57.7 | 10.9 | 67.7 | 30.6 | 81.7 | 85.1 | 79.9 | 4.6 | 81.5 |

| POSITION OF FR1 OF LIGHT CHAIN | L21 | L22 | L23 |
|---|---|---|---|
| TOTAL VALUE OF AMINO ACID FREQUENCIES (%) | 1.5 | 91.1 | 0.2 |
| RATIO OF SOLVENT-EXPOSED SURFACE AREA (%) | 1.5 | 25.7 | 0.0 |

FIG. 4

| POSITION OF FR1 OF LIGHT CHAIN | L1 | L2 | L3 | L4 | L5 | L6 | L7 | L8 | L9 | L10 |
|---|---|---|---|---|---|---|---|---|---|---|
| TOTAL VALUE OF AMINO ACID FREQUENCIES (%) | 62.9 | 27.7 | 67.8 | 8.2 | 93.8 | 4.9 | 66.2 | 9.1 | 63.2 | 83.5 |
| RATIO OF SOLVENT-EXPOSED SURFACE AREA (%) | 69.0 | 7.1 | 88.1 | 0.0 | 84.8 | 0.0 | 100.0 | 54.8 | 111.5 | 74.0 |

| POSITION OF FR1 OF LIGHT CHAIN | L11 | L12 | L13 | L14 | L15 | L16 | L17 | L18 | L19 | L20 |
|---|---|---|---|---|---|---|---|---|---|---|
| TOTAL VALUE OF AMINO ACID FREQUENCIES (%) | 30.3 | 83.1 | 37.5 | 81.6 | 23.2 | 1.4 | 58.1 | 80.0 | 61.4 | 93.5 |
| RATIO OF SOLVENT-EXPOSED SURFACE AREA (%) | 26.8 | 57.7 | 10.9 | 67.7 | 30.6 | 81.7 | 85.1 | 79.9 | 4.6 | 81.5 |

| POSITION OF FR1 OF LIGHT CHAIN | L21 | L22 | L23 |
|---|---|---|---|
| TOTAL VALUE OF AMINO ACID FREQUENCIES (%) | 1.5 | 91.1 | 0.2 |
| RATIO OF SOLVENT-EXPOSED SURFACE AREA (%) | 1.5 | 25.7 | 0.0 |

DIQMTQSPSSLSASVGDRVTITCRASQDVNTAVAWYQQKPGKAPKLLIYSASF
LYSGVPSRFSGSRSGTDFTLTISSLQPEDFATYYCQQHYTTPPTFGQGTKVEI
KRTVAAPSVFIFPPSDEQLKSGTASVVCLLNNFYPREAKVQWKVDNALQSGN
SQESVTEQDSKDSTYSLSSTLTLSKADYEKHKVYACEVTHQGLSSPVTKSFNR
GEC (SEQ ID NO: 35)

FIG. 10B

EVQLVESGGGLVQPGGSLRLSCAASGFNIKDTYIHWVRQAPGKGLEWVARIY
PTNGYTRYADSVKGRFTISADTSKNTAYLQMNSLRAEDTAVYYCSRWGGDGF
YAMDYWGQGTLVTVSSASTKGPSVFPLAPSSKSTSGGTAALGCLVKDYFPEP
VTVSWNSGALTSGVHTFPAVLQSSGLYSLSSVVTVPSSSLGTQTYICNVNHKP
SNTKVDKKVEPKSCDKTHTCPPCPAPELLGGPSVFLFPPKPKDTLMISRTPEV
TCVVVDVSHEDPEVKFNWYVDGVEVHNAKTKPREEQYNSTYRVVSVLTVLH
QDWLNGKEYKCKVSNKALPAPIEKTISKAKGQPREPQVYTLPPSREEMTKNQ
VSLTCLVKGFYPSDIAVEWESNGQPENNYKTTPPVLDSDGSFFLYSKLTVDKS
RWQQGNVFSCSVMHEALHNHYTQKSLSLSPGK (SEQ ID NO: 36)

FIG. 10C

EVQLVESGGGLVQPGGSLRLSCAASGFNIKDTYIHWVRQAPGKGLEWVARIY
PTNGYTRYADSVKGRFTISADTSKNTAYLQMNSLRAEDTAVYYCSRWGGDGF
YAMDYWGQGTLVTVSSASTKGPSVFPLAPSSKSTSGGTAALGCLVKDYFPEP
VTVSWNSGALTSGVHTFPAVLQSSGLYSLSSVVTVPSSSLGTQTYICNVNHKP
SNTKVDKKVEPKSC (SEQ ID NO: 37)

SEQUENCE LISTING

```
Sequence total quantity: 52
SEQ ID NO: 1           moltype = DNA  length = 39
FEATURE                Location/Qualifiers
misc_feature           1..39
                       note = primer
source                 1..39
                       mol_type = other DNA
                       organism = synthetic construct
SEQUENCE: 1
agaaccagaa gcccggcgac cctctcggtc acccccggc                            39

SEQ ID NO: 2           moltype = DNA  length = 32
FEATURE                Location/Qualifiers
misc_feature           1..32
                       note = primer
source                 1..32
                       mol_type = other DNA
                       organism = synthetic construct
```

```
SEQUENCE: 2
agagcagagc gaccctctcg gtcaccccg gc                                              32

SEQ ID NO: 3              moltype = DNA   length = 29
FEATURE                   Location/Qualifiers
misc_feature              1..29
                          note = primer
source                    1..29
                          mol_type = other DNA
                          organism = synthetic construct
SEQUENCE: 3
gcccgcgcac cctctcggtc accccggc                                                  29

SEQ ID NO: 4              moltype = DNA   length = 33
FEATURE                   Location/Qualifiers
misc_feature              1..33
                          note = primer
source                    1..33
                          mol_type = other DNA
                          organism = synthetic construct
SEQUENCE: 4
ccctctcgag aaccccggc aactcggtgt cgc                                             33

SEQ ID NO: 5              moltype = DNA   length = 39
FEATURE                   Location/Qualifiers
misc_feature              1..39
                          note = primer
source                    1..39
                          mol_type = other DNA
                          organism = synthetic construct
SEQUENCE: 5
ggcaactcgg tgtcgctccg ctgccgcgcc tcgcagtcg                                      39

SEQ ID NO: 6              moltype = DNA   length = 36
FEATURE                   Location/Qualifiers
misc_feature              1..36
                          note = primer
source                    1..36
                          mol_type = other DNA
                          organism = synthetic construct
SEQUENCE: 6
aactcgcgat cgctctcgtg ccgcgcctcg cagtcg                                         36

SEQ ID NO: 7              moltype = DNA   length = 36
FEATURE                   Location/Qualifiers
misc_feature              1..36
                          note = primer
source                    1..36
                          mol_type = other DNA
                          organism = synthetic construct
SEQUENCE: 7
gtgtcgcgat cgcgacgcgc ctcgcagtcg atcggc                                         36

SEQ ID NO: 8              moltype = DNA   length = 21
FEATURE                   Location/Qualifiers
misc_feature              1..21
                          note = primer
source                    1..21
                          mol_type = other DNA
                          organism = synthetic construct
SEQUENCE: 8
ctctcgtgcc gcgcctcgca g                                                         21

SEQ ID NO: 9              moltype = DNA   length = 27
FEATURE                   Location/Qualifiers
misc_feature              1..27
                          note = primer
source                    1..27
                          mol_type = other DNA
                          organism = synthetic construct
SEQUENCE: 9
cgctgccgcg cctcgcagtc gatcggc                                                   27

SEQ ID NO: 10             moltype = DNA   length = 30
FEATURE                   Location/Qualifiers
misc_feature              1..30
                          note = primer
source                    1..30
                          mol_type = other DNA
```

```
                        organism = synthetic construct
SEQUENCE: 10
agatcgagac gcgcctcgca gtcgatcggc                                       30

SEQ ID NO: 11           moltype = DNA   length = 21
FEATURE                 Location/Qualifiers
misc_feature            1..21
                        note = primer
source                  1..21
                        mol_type = other DNA
                        organism = synthetic construct
SEQUENCE: 11
ggcaccgact tcaccctgtc g                                                21

SEQ ID NO: 12           moltype = DNA   length = 33
FEATURE                 Location/Qualifiers
misc_feature            1..33
                        note = primer
source                  1..33
                        mol_type = other DNA
                        organism = synthetic construct
SEQUENCE: 12
gactctatct cctctggaca ttatgactga ggc                                   33

SEQ ID NO: 13           moltype = DNA   length = 40
FEATURE                 Location/Qualifiers
misc_feature            1..40
                        note = primer
source                  1..40
                        mol_type = other DNA
                        organism = synthetic construct
SEQUENCE: 13
gggttctgac tctatctcct ctggacatta tgactgaggc                            40

SEQ ID NO: 14           moltype = DNA   length = 35
FEATURE                 Location/Qualifiers
misc_feature            1..35
                        note = primer
source                  1..35
                        mol_type = other DNA
                        organism = synthetic construct
SEQUENCE: 14
tctggcgcag gcggatatct cctctggaca ttatg                                 35

SEQ ID NO: 15           moltype = DNA   length = 44
FEATURE                 Location/Qualifiers
misc_feature            1..44
                        note = primer
source                  1..44
                        mol_type = other DNA
                        organism = synthetic construct
SEQUENCE: 15
tcgctctgct ctgggttctg acgatatctc ctctggacat tatg                       44

SEQ ID NO: 16           moltype = DNA   length = 53
FEATURE                 Location/Qualifiers
misc_feature            1..53
                        note = primer
source                  1..53
                        mol_type = other DNA
                        organism = synthetic construct
SEQUENCE: 16
gggggtgacc gagagggtgc gcgggctctg gcgcaggacg atatctcctc tgg             53

SEQ ID NO: 17           moltype = DNA   length = 35
FEATURE                 Location/Qualifiers
misc_feature            1..35
                        note = primer
source                  1..35
                        mol_type = other DNA
                        organism = synthetic construct
SEQUENCE: 17
tcggggggtt cgcgagaggg tcgccgggct ctggg                                 35

SEQ ID NO: 18           moltype = DNA   length = 30
FEATURE                 Location/Qualifiers
misc_feature            1..30
                        note = primer
source                  1..30
```

```
                        mol_type = other DNA
                        organism = synthetic construct
SEQUENCE: 18
cgagtttcgg ggggtgaccg agagggtcgc                                    30

SEQ ID NO: 19           moltype = DNA   length = 32
FEATURE                 Location/Qualifiers
misc_feature            1..32
                        note = primer
source                  1..32
                        mol_type = other DNA
                        organism = synthetic construct
SEQUENCE: 19
gcgcacgcgg cggccggggg tgaccgagag gg                                 32

SEQ ID NO: 20           moltype = DNA   length = 35
FEATURE                 Location/Qualifiers
misc_feature            1..35
                        note = primer
source                  1..35
                        mol_type = other DNA
                        organism = synthetic construct
SEQUENCE: 20
gaggcgcacg cggttgccgg gggtgaccga gaggg                              35

SEQ ID NO: 21           moltype = DNA   length = 32
FEATURE                 Location/Qualifiers
misc_feature            1..32
                        note = primer
source                  1..32
                        mol_type = other DNA
                        organism = synthetic construct
SEQUENCE: 21
cgatctcgag ttgccggggg tgaccgagag gg                                 32

SEQ ID NO: 22           moltype = DNA   length = 35
FEATURE                 Location/Qualifiers
misc_feature            1..35
                        note = primer
source                  1..35
                        mol_type = other DNA
                        organism = synthetic construct
SEQUENCE: 22
tctgcctctg cctctgaagc gcgacgggat ccccg                              35

SEQ ID NO: 23           moltype = DNA   length = 28
FEATURE                 Location/Qualifiers
misc_feature            1..28
                        note = primer
source                  1..28
                        mol_type = other DNA
                        organism = synthetic construct
SEQUENCE: 23
gaggctcggg caccgacttc accctgtc                                      28

SEQ ID NO: 24           moltype = DNA   length = 48
FEATURE                 Location/Qualifiers
misc_feature            1..48
                        note = primer
source                  1..48
                        mol_type = other DNA
                        organism = synthetic construct
SEQUENCE: 24
tcgggcaccg acttcaccct gtcgatcaga agagtcgaga cggaggac                48

SEQ ID NO: 25           moltype = DNA   length = 32
FEATURE                 Location/Qualifiers
misc_feature            1..32
                        note = primer
source                  1..32
                        mol_type = other DNA
                        organism = synthetic construct
SEQUENCE: 25
ccagattcac cctgtcgatc aacagcgtcg ag                                 32

SEQ ID NO: 26           moltype = DNA   length = 34
FEATURE                 Location/Qualifiers
misc_feature            1..34
                        note = primer
```

```
source                          1..34
                                mol_type = other DNA
                                organism = synthetic construct
SEQUENCE: 26
ccagattcag actgtcgatc aacagcgtcg agac                                    34

SEQ ID NO: 27                   moltype = DNA   length = 21
FEATURE                         Location/Qualifiers
misc_feature                    1..21
                                note = primer
source                          1..21
                                mol_type = other DNA
                                organism = synthetic construct
SEQUENCE: 27
agtcgagacg gaggacttcg g                                                  21

SEQ ID NO: 28                   moltype = DNA   length = 30
FEATURE                         Location/Qualifiers
misc_feature                    1..30
                                note = primer
source                          1..30
                                mol_type = other DNA
                                organism = synthetic construct
SEQUENCE: 28
agaacgagag acttcggcat gtacttctgc                                         30

SEQ ID NO: 29                   moltype = DNA   length = 32
FEATURE                         Location/Qualifiers
misc_feature                    1..32
                                note = primer
source                          1..32
                                mol_type = other DNA
                                organism = synthetic construct
SEQUENCE: 29
tgcctctgaa gcgtctcggg atccccgaga tc                                      32

SEQ ID NO: 30                   moltype = DNA   length = 37
FEATURE                         Location/Qualifiers
misc_feature                    1..37
                                note = primer
source                          1..37
                                mol_type = other DNA
                                organism = synthetic construct
SEQUENCE: 30
gcccgagccg ctgaagcgtc tcgggatccc cgagatc                                 37

SEQ ID NO: 31                   moltype = DNA   length = 24
FEATURE                         Location/Qualifiers
misc_feature                    1..24
                                note = primer
source                          1..24
                                mol_type = other DNA
                                organism = synthetic construct
SEQUENCE: 31
tgcctctgcc tctgccgctg aagc                                               24

SEQ ID NO: 32                   moltype = DNA   length = 23
FEATURE                         Location/Qualifiers
misc_feature                    1..23
                                note = primer
source                          1..23
                                mol_type = other DNA
                                organism = synthetic construct
SEQUENCE: 32
tgcctctgcc cgagccgctg aag                                                23

SEQ ID NO: 33                   moltype = DNA   length = 24
FEATURE                         Location/Qualifiers
misc_feature                    1..24
                                note = primer
source                          1..24
                                mol_type = other DNA
                                organism = synthetic construct
SEQUENCE: 33
cttctgattc tcagggtgaa gtcg                                               24

SEQ ID NO: 34                   moltype = DNA   length = 28
FEATURE                         Location/Qualifiers
misc_feature                    1..28
```

```
                                  note = primer
source                            1..28
                                  mol_type = other DNA
                                  organism = synthetic construct
SEQUENCE: 34
gactctgttg atcgacaggg tgaagtcg                                              28

SEQ ID NO: 35                     moltype = AA  length = 214
FEATURE                           Location/Qualifiers
REGION                            1..214
                                  note = humanized antibody
source                            1..214
                                  mol_type = protein
                                  organism = synthetic construct
SEQUENCE: 35
DIQMTQSPSS LSASVGDRVT ITCRASQDVN TAVAWYQQKP GKAPKLLIYS ASFLYSGVPS            60
RFSGSRSGTD FTLTISSLQP EDFATYYCQQ HYTTPPTFGQ GTKVEIKRTV AAPSVFIFPP           120
SDEQLKSGTA SVVCLLNNFY PREAKVQWKV DNALQSGNSQ ESVTEQDSKD STYSLSSTLT           180
LSKADYEKHK VYACEVTHQG LSSPVTKSFN RGEC                                       214

SEQ ID NO: 36                     moltype = AA  length = 450
FEATURE                           Location/Qualifiers
REGION                            1..450
                                  note = humanized antibody
source                            1..450
                                  mol_type = protein
                                  organism = synthetic construct
SEQUENCE: 36
EVQLVESGGG LVQPGGSLRL SCAASGFNIK DTYIHWVRQA PGKGLEWVAR IYPTNGYTRY            60
ADSVKGRFTI SADTSKNTAY LQMNSLRAED TAVYYCSRWG GDGFYAMDYW GQGTLVTVSS           120
ASTKGPSVFP LAPSSKSTSG GTAALGCLVK DYFPEPVTVS WNSGALTSGV HTFPAVLQSS           180
GLYSLSSVVT VPSSSLGTQT YICNVNHKPS NTKVDKKVEP KSCDKTHTCP PCPAPELLGG           240
PSVFLFPPKP KDTLMISRTP EVTCVVVDVS HEDPEVKFNW YVDGVEVHNA KTKPREEQYN           300
STYRVVSVLT VLHQDWLNGK EYKCKVSNKA LPAPIEKTIS KAKGQPREPQ VYTLPPSREE           360
MTKNQVSLTC LVKGFYPSDI AVEWESNGQP ENNYKTTPPV LDSDGSFFLY SKLTVDKSRW           420
QQGNVFSCSV MHEALHNHYT QKSLSLSPGK                                            450

SEQ ID NO: 37                     moltype = AA  length = 223
FEATURE                           Location/Qualifiers
REGION                            1..223
                                  note = humanized antibody
source                            1..223
                                  mol_type = protein
                                  organism = synthetic construct
SEQUENCE: 37
EVQLVESGGG LVQPGGSLRL SCAASGFNIK DTYIHWVRQA PGKGLEWVAR IYPTNGYTRY            60
ADSVKGRFTI SADTSKNTAY LQMNSLRAED TAVYYCSRWG GDGFYAMDYW GQGTLVTVSS           120
ASTKGPSVFP LAPSSKSTSG GTAALGCLVK DYFPEPVTVS WNSGALTSGV HTFPAVLQSS           180
GLYSLSSVVT VPSSSLGTQT YICNVNHKPS NTKVDKKVEP KSC                             223

SEQ ID NO: 38                     moltype = AA  length = 11
FEATURE                           Location/Qualifiers
REGION                            1..11
                                  note = humanized antibody
source                            1..11
                                  mol_type = protein
                                  organism = synthetic construct
SEQUENCE: 38
RASQDVNTAV A                                                                 11

SEQ ID NO: 39                     moltype = AA  length = 7
FEATURE                           Location/Qualifiers
REGION                            1..7
                                  note = humanized antibody
source                            1..7
                                  mol_type = protein
                                  organism = synthetic construct
SEQUENCE: 39
SASFLYS                                                                       7

SEQ ID NO: 40                     moltype = AA  length = 9
FEATURE                           Location/Qualifiers
REGION                            1..9
                                  note = humanized antibody
source                            1..9
                                  mol_type = protein
                                  organism = synthetic construct
SEQUENCE: 40
QQHYTTPPT                                                                     9
```

```
SEQ ID NO: 41             moltype = AA   length = 110
FEATURE                   Location/Qualifiers
REGION                    1..110
                          note = humanized antibody
source                    1..110
                          mol_type = protein
                          organism = synthetic construct
SEQUENCE: 41
DIQMTQSPSS LSASVGDRVT ITCRASQDVN TAVAWYQQKP GKAPKLLIYS ASFLYSGVPS    60
RFSGSRSGTD FTLTISSLQP EDFATYYCQQ HYTTPPTFGQ GTKVEIKRTV              110

SEQ ID NO: 42             moltype = AA   length = 5
FEATURE                   Location/Qualifiers
REGION                    1..5
                          note = humanized antibody
source                    1..5
                          mol_type = protein
                          organism = synthetic construct
SEQUENCE: 42
DTYIH                                                                 5

SEQ ID NO: 43             moltype = AA   length = 17
FEATURE                   Location/Qualifiers
REGION                    1..17
                          note = humanized antibody
source                    1..17
                          mol_type = protein
                          organism = synthetic construct
SEQUENCE: 43
RIYPTNGYTR YADSVKG                                                   17

SEQ ID NO: 44             moltype = AA   length = 11
FEATURE                   Location/Qualifiers
REGION                    1..11
                          note = humanized antibody
source                    1..11
                          mol_type = protein
                          organism = synthetic construct
SEQUENCE: 44
WGGDGFYAMD Y                                                         11

SEQ ID NO: 45             moltype = AA   length = 120
FEATURE                   Location/Qualifiers
REGION                    1..120
                          note = humanized antibody
source                    1..120
                          mol_type = protein
                          organism = synthetic construct
SEQUENCE: 45
EVQLVESGGG LVQPGGSLRL SCAASGFNIK DTYIHWVRQA PGKGLEWVAR IYPTNGYTRY    60
ADSVKGRFTI SADTSKNTAY LQMNSLRAED TAVYYCSRWG GDGFYAMDYW GQGTLVTVSS   120

SEQ ID NO: 46             moltype = DNA   length = 37
FEATURE                   Location/Qualifiers
misc_feature              1..37
                          note = primer
source                    1..37
                          mol_type = other DNA
                          organism = synthetic construct
SEQUENCE: 46
catctgcacc aatcaccgca cattatgtcc gcatctc                             37

SEQ ID NO: 47             moltype = DNA   length = 34
FEATURE                   Location/Qualifiers
misc_feature              1..34
                          note = primer
source                    1..34
                          mol_type = other DNA
                          organism = synthetic construct
SEQUENCE: 47
tatgtcccct ctgctcataa tcacagaggc actg                                34

SEQ ID NO: 48             moltype = DNA   length = 37
FEATURE                   Location/Qualifiers
misc_feature              1..37
                          note = primer
source                    1..37
                          mol_type = other DNA
```

```
                        organism = synthetic construct
SEQUENCE: 48
aaggccaaga ttaagtgcag atctaatcag agcgttg                              37

SEQ ID NO: 49           moltype = DNA  length = 29
FEATURE                 Location/Qualifiers
misc_feature            1..29
                        note = primer
source                  1..29
                        mol_type = other DNA
                        organism = synthetic construct
SEQUENCE: 49
atctccaaga ctgacaggca gggagagtg                                       29

SEQ ID NO: 50           moltype = DNA  length = 29
FEATURE                 Location/Qualifiers
misc_feature            1..29
                        note = primer
source                  1..29
                        mol_type = other DNA
                        organism = synthetic construct
SEQUENCE: 50
cagccgagag acttcgccac gtattactg                                       29

SEQ ID NO: 51           moltype = DNA  length = 32
FEATURE                 Location/Qualifiers
misc_feature            1..32
                        note = primer
source                  1..32
                        mol_type = other DNA
                        organism = synthetic construct
SEQUENCE: 51
cagtcttctg atcgtcaggg taaaatcggt ac                                   32

SEQ ID NO: 52           moltype = AA  length = 214
FEATURE                 Location/Qualifiers
REGION                  1..214
                        note = modified antibody
source                  1..214
                        mol_type = protein
                        organism = synthetic construct
SEQUENCE: 52
DIQMTQSPSS LSASVGDRVT ITCRASQDVN TAVAWYQQKP GKAPKLLIYS ASFLYSGVPS      60
RFSGSRSGTD FTLTIRRLQP RDFATYYCQQ HYTTPPTFGQ GTKVEIKRTV AAPSVFIFPP     120
SDEQLKSGTA SVVCLLNNFY PREAKVQWKV DNALQSGNSQ ESVTEQDSKD STYSLSSTLT     180
LSKADYEKHK VYACEVTHQG LSSPVTKSFN RGEC                                 214
```

METHOD FOR IMPROVING AFFINITY OF ANTIBODY FOR ANTIGEN AND USE THEREOF

CROSS REFERENCE TO RELATED APPLICATIONS

This application is a Rule 53 (b) Continuation of U.S. application Ser. No. 17/154,297 filed Jan. 21, 2021, which claims priority to Japanese Patent Application No. 2020-10411, filed on Jan. 24, 2020, Japanese Patent Application No. 2020-010413, filed on Jan. 24, 2020, Japanese Patent Application No. 2020-010414, filed on Jan. 24, 2020, Japanese Patent Application No. 2020-010416, filed on Jan. 24, 2020, Japanese Patent Application No. 2020-010417, filed on Jan. 24, 2020, Japanese Patent Application No. 2020-010418, filed on Jan. 24, 2020, Japanese Patent Application No. 2020-010419, filed on Jan. 24, 2020, Japanese Patent Application No. 2020-010420, filed on Jan. 24, 2020, Japanese Patent Application No. 2020-093384, filed on May 28, 2020, Japanese Patent Application No. 2020-093389, filed on May 28, 2020, Japanese Patent Application No. 2020-093392, filed on May 28, 2020, Japanese Patent Application No. 2020-093399, filed on May 28, 2020, Japanese Patent Application No. 2020-093405, filed on May 28, 2020, Japanese Patent Application No. 2020-093411, filed on May 28, 2020, Japanese Patent Application No. 2020-093421, filed on May 28, 2020, and Japanese Patent Application No. 2020-093424, filed on May 28, 2020, entitled "METHOD FOR IMPROVING AFFINITY OF ANTIBODY FOR ANTIGEN AND USE THEREOF".

INCORPORATION BY REFERENCE OF SEQUENCE LISTING

The content of the electronically submitted sequence listing, file name: Q282521_sequence listing as filed.xml; size: 66.1 kilobytes; and date of creation: Jan. 19, 2023, filed herewith, is incorporated herein by reference in its entirety.

FIELD OF THE INVENTION

The present invention relates to a method for improving affinity of an antibody for an antigen. The present invention relates to a method for producing an antibody with improved affinity for an antigen as compared to an unmodified antibody. The present invention relates to a modified antibody with improved affinity for an antigen as compared to an unmodified antibody.

BACKGROUND

Conventionally, a technique for changing affinity of an antibody for an antigen by modifying an amino acid sequence of the antibody has been known. For example, U.S. Patent Application Publication No. 2018/0179298 describes a method for controlling affinity for an antigen by changing at least 3 amino acid residues in framework region 3 of an antibody to charged amino acid residues. In this method, the affinity of the antibody for an antigen is improved while maintaining an amino acid sequence of complementarity determining region (CDR).

An object of the present invention is to provide a novel method for improving affinity of the antibody for an antigen by modifying amino acid residues of a framework region (FR) without modifying the amino acid sequence of CDR, and a novel antibody with improved affinity for an antigen.

SUMMARY OF THE INVENTION

The scope of the present invention is defined solely by the appended claims, and is not affected to any degree by the statements within this summary.

The present inventors have found that total value of amino acid frequencies of predetermined amino acid residues at each position of an amino acid sequence of FR of a light chain of an antibody and a ratio of solvent-exposed surface area of each amino acid residue in the FR are involved in affinity of the antibody for an antigen, thereby completing the present invention.

The present invention provides a method for improving affinity of an antibody for an antigen, comprising: by changing 18th, 20th and 22nd amino acid residues of a light chain in unmodified antibody, the positions of the amino acid residues being defined by Kabat method, to charged amino acid residues, improving affinity for an antigen as compared to the unmodified antibody.

The present invention provides a method for producing an antibody with improved affinity for an antigen as compared to an unmodified antibody, including changing at least 3 amino acid residues selected from a group consisting of 18th, 20th and 22nd amino acid residues of a light chain in the unmodified antibody, the positions of the amino acid residues being defined by Kabat method, to charged amino acid residues, and recovering the antibody obtained in the changing.

The present invention provides a modified antibody with improved affinity for an antigen as compared to an unmodified antibody. In this modified antibody, at least 3 amino acid residues selected from a group consisting of 18th, 20th and 22nd amino acid residues of a light chain defined by Kabat method in the unmodified antibody are changed to charged amino acid residues.

In certain embodiments, the charged amino acid residue is a basic amino acid residue.

In certain embodiments, the antibody is an antibody fragment.

In certain embodiments, the antibody fragment is a Fab fragment, a F(ab')2 fragment, a Fab' fragment, a Fd fragment, a Fv fragment, a dAb fragment, scFv, or rIgG.

BRIEF DESCRIPTION OF THE DRAWINGS

FIG. 4 is a diagram showing an example of a display screen of analysis results;

FIG. 6 is a diagram showing an example of a display screen of analysis results;

FIG. 10A is a light chain of wild-type humanized anti-HER2 antibody.

FIG. 10B is a heavy chain of wild-type humanized anti-HER2 antibody.

FIG. 10C is a heavy chain of Fab fragment of wild-type humanized anti-HER2 antibody.

DETAILED DESCRIPTION OF THE PREFERRED EMBODIMENTS

Figure 1:
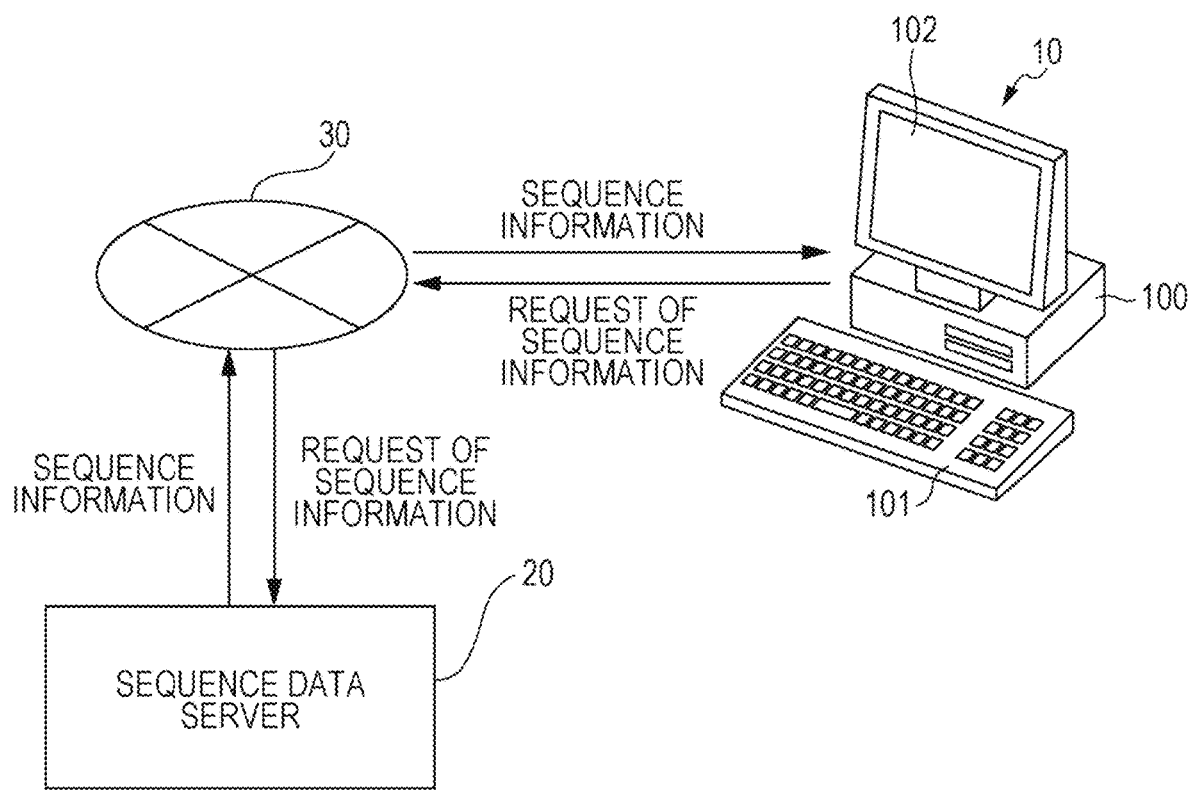
FIG. 1 is a schematic diagram of an amino acid sequence analysis system.

1. Method for Improving Affinity of Antibody for Antigen

In the method for improving affinity of an antibody for an antigen of the present embodiment (hereinafter, also referred to as "method for improving affinity"), among amino acid residues satisfying predetermined conditions in an amino acid sequence of FR of a light chain of an antibody, at least 3 amino acid residues are changed to charged amino acid residues. As a result, the affinity of the antibody for an antigen is improved as compared to that of an unmodified antibody. Here, an original antibody whose affinity for an antigen is improved by the method provided by the present disclosure described above is referred to as an "unmodified antibody". As used herein, the term "unmodified antibody" means an antibody having an amino acid sequence before applying the "method for improving affinity". The "unmodified antibody" includes not only an antibody having a natural amino acid sequence (wild-type antibody) but also an antibody in which the amino acid sequence is artificially changed based on a method other than the "method for improving affinity".

In the present embodiment, the unmodified antibody is not particularly limited. Since it is not necessary to change the amino acid sequence of CDR in the method for improving affinity of the present embodiment, an antibody that recognizes any antigen may be used. In a preferred embodiment, the unmodified antibody is an antibody in which a base sequence of a gene encoding a variable region of light chain is known or an antibody in which the base sequence can be confirmed. Specifically, it is an antibody in which a base sequence of an antibody gene is disclosed in a known database, or an antibody in which a hybridoma producing the antibody is available. Examples of the database include GenBank, abYsis, IMGT, and the like. The antibody class may be IgG, IgA, IgM, IgD or IgE, and is preferably IgG. The unmodified antibody may be in a form of an antibody fragment as long as it has a variable region including FR. Examples of the antibody fragment include Fab fragments, F(ab')2 fragments, Fab' fragments, Fd fragments, Fv fragments, dAb fragments, single chain antibodies (scFv), reduced IgG (rIgG), and the like. Among them, Fab fragments are particularly preferred.

As an example of the unmodified antibody, amino acid sequences of a light chain and a heavy chain of a humanized anti-HER2 antibody (trastuzumab) and an amino acid sequence of a heavy chain of a Fab fragment are shown in FIGS. 10A-10C, respectively. In FIGS. 10A-10C, the underlined parts indicate a variable region, and the gray marker parts indicate CDRs.

The amino acid sequences of each CDR and variable region of the light chain of the wild-type humanized anti-HER2 antibody are as follows.

Light chain CDR1:
(SEQ ID NO: 38)
RASQDVNTAVA

Light chain CDR2:
(SEQ ID NO: 39)
SASFLYS

Light chain CDR3:
(SEQ ID NO: 40)
QQHYTTPPT

Variable region:
(SEQ ID NO: 41)
DIQMTQSPSSLSASVGDRVTITCRASQDVNTAVAWYQQKPGKAPKLLIY
SASFLYSGVPSRFSGSRSGTDFTLTISSLQPEDFATYYCQQHYTTPPTF
GQGTKVEIKRTV The amino acid sequences of each CDR and variable region of the heavy chain of the wild-type humanized anti-HER2 antibody are as follows.

Heavy chain CDR1:
(SEQ ID NO: 42)
DTYIH

Heavy chain CDR2:
(SEQ ID NO: 43)
RIYPTNGYTRYADSVKG

Heavy chain CDR3:
(SEQ ID NO: 44)
WGGDGFYAMDY

Variable region:
(SEQ ID NO: 45)
EVQLVESGGGLVQPGGSLRLSCAASGFNIKDTYIHWVRQAPGKGLEWVA
RIYPTNGYTRYADSVKGRFTISADTSKNTAYLQMNSLRAEDTAVYYCSR
WGGDGFYAMDYWGQGTLVTVSS The framework region (FR) is a region other than the CDRs present in each variable region of the light chain and heavy chain of the antibody. FR plays a role of a scaffold linking the three CDRs and contributes to structural stability of the CDR. Therefore, the amino acid sequence of FR is highly conserved between antibodies of the same species. Each variable region of the light chain and heavy chain has three CDRs, CDR1, CDR2 and CDR3, and four FRs, FR1, FR2, FR3 and FR4. These are arranged in the order of FR1, CDR1, FR2, CDR2, FR3, CDR3 and FR4 from the N-terminal side of the variable region. Hereinafter, when referring to FR of an antibody, unless otherwise specified, the terms "framework region" and "FR" mean FR of a light chain.

In the method for improving affinity of the present embodiment, at least 3 of the amino acid residues satisfying predetermined conditions in the amino acid sequence of FR of a light chain of an unmodified antibody are changed to charged amino acid residues. The amino acid residue satisfying predetermined conditions is an amino acid residue satisfying both following conditions (1) and (2).

(1) In the amino acid sequence of FR of a light chain of an unmodified antibody, present at positions where total value of amino acid frequencies of arginine, serine, threonine, valine, aspartic acid and glutamic acid is 35% or more.

(2) In the amino acid sequence of FR of a light chain of an unmodified antibody, has a ratio of solvent-exposed surface area of 20% or more.

In the present specification, in an unmodified antibody, changing an amino acid residue satisfying the above conditions (1) and (2) to a charged amino acid residue is also referred to as "modify" or "modification". Hereinafter, an antibody obtained by modifying an unmodified antibody by the method for improving affinity of the present embodiment is also referred to as a "modified antibody".

Since the CDR is involved in specificity of the antibody, it is preferable that the amino acid sequence of CDR is not changed in the method for improving affinity of the present embodiment. That is, the amino acid sequence of the CDR of the modified antibody is preferably the same as the amino acid sequence of the CDR of the unmodified antibody.

In the present embodiment, the affinity of the modified antibody for an antigen may be evaluated by a kinetic parameter in an antigen-antibody reaction or may be evaluated by an immunological measurement method such as an ELISA method. Examples of the kinetic parameter include dissociation constant (Kd), binding rate constant (kon), and dissociation rate constant (koff). Among them, Kd is preferable. The kinetic parameter in an antigen-antibody reaction can be obtained by surface plasmon resonance (SPR) technology or the like. The value of Kd in the antigen-antibody reaction of the modified antibody is, for example, about ½, about ⅕, about 1/10, about 1/20, about 1/50, about 1/100 or about 1/1000, as compared to the unmodified antibody.

As used herein, the term "position" refers to a position of an amino acid residue in an amino acid sequence. In the present embodiment, the position in the amino acid sequence of FR is a position in the amino acid sequence of FR defined by a method of numbering amino acid residues of CDR (hereinafter, also referred to as "numbering method"). The numbering method is a method for defining boundary and length of CDR and is known in the art. When the amino acid residues of CDR are numbered by the numbering method, the amino acid residues of FR are also numbered. In the present embodiment, the position in the amino acid sequence of FR is indicated by the number assigned by the numbering method. As used herein, "Ln" (where n is a positive integer) represents the nth position in a light chain amino acid sequence. For example, L1 means a first position of the light chain amino acid sequence, and L2 means a second position of the light chain amino acid sequence.

Examples of the numbering method include Kabat method (Kabat E A. et al., Sequences of Proteins of Immunological Interest., NIH publication No. 91-3242), Chothia method (Chothia C. and Lesk A M., Canonical Structures for the Hypervariable Regions of Immunoglobulins., J Mol Biol., vol. 196, p. 901-917, 1987), IMGT method (Lefranc M P. et al., Developmental and Comparative Immunology 29 (2005) 185-203), Honergger method (Honegger A. et al., Yet Another Numbering Scheme for Immunoglobulin Variable Domains: An Automatic Modeling and Analysis Tool., J Mol Biol., vol. 309, p. 657-670, 2001), ABM method, Contact method, and the like. In the present embodiment, the FR of an antibody may be defined by any numbering method, but is preferably defined by the Kabat method. In the unmodified antibody, in the Kabat method, FR1 of the light chain is defined as a region consisting of 1st to 23rd amino acid residues of the light chain, FR2 of the light chain is defined as a region consisting of 35th to 49th amino acid residues of the light chain, FR3 of the light chain is defined as a region consisting of 57th to 88th amino acid residues of the light chain, and FR4 of the light chain is defined as a region consisting of 98th to 109th amino acid residues of the light chain.

Amino acid frequency is also called amino acid appearance frequency, and refers to a ratio indicating how much predetermined amino acid appears at each position of a plurality of amino acid sequences when aligning these amino acid sequences. The amino acid frequency itself is a known index. Amino acid sequence alignment means aligning a plurality of amino acid sequences in a comparable manner. Amino acid sequence alignment can be performed by, for example, a known multiple alignment program such as ClustalW or TREBMAL. A method for calculating amino acid frequency itself is known, and amino acid frequency can be calculated by the above multiple alignment program or the like. Amino acid sequence alignment and amino acid frequency calculation can also be performed by abYsis. abYsis can be used not only as a database to provide antibody sequences, but also as software for analyzing and predicting antibody sequences, structures and functions. For example, when an amino acid appears in all of a plurality of amino acid sequences at a predetermined position of the plurality of aligned amino acid sequences, amino acid frequency of the amino acid at that position is 100%. When an amino acid appears in half of a plurality of amino acid sequences at a predetermined position of the plurality of aligned amino acid sequences, amino acid frequency of the amino acid at that position is 50%. When an amino acid never appears at a predetermined position of a plurality of aligned amino acid sequences, amino acid frequency of the amino acid at that position is 0%.

In the present embodiment, amino acid sequences of light chains of a plurality of reference antibodies are obtained in order to specify amino acid residues satisfying the above condition (1) in the FR of an unmodified antibody. By aligning the obtained amino acid sequences of light chains of a plurality of reference antibodies, amino acid frequencies at each position in an amino acid sequence of FRs of light chains of reference antibodies can be obtained. Amino acid frequencies at each position obtained from the plurality of reference antibodies can be used as amino acid frequencies at corresponding positions in the amino acid sequence of a light chain of an unmodified antibody. The reference antibody is not particularly limited as long as it is an antibody having an amino acid sequence different from that of the unmodified antibody. The reference antibody is preferably the same type of antibody as the unmodified antibody, since the amino acid sequence of FR of the antibody is highly conserved among antibodies of the same type. The amino acid sequence of a light chain of a reference antibody can be obtained from a known database such as GenBank, abYsis, and IMGT. The number of the amino acid sequence of a light chain of a reference antibody is not particularly limited, but is, for example, 1000 or more, and preferably 10000 or more. The amino acid sequences of light chains of a plurality of reference antibodies to be obtained may be amino acid sequences of the entire light chains or amino acid sequences of a part of the light chains. The amino acid sequence of a part of the light chain preferably contains an amino acid sequence of FR1 and/or FR3.

By aligning the obtained amino acid sequences of light chains of a plurality of reference antibodies, respective amino acid frequencies of arginine (R), serine (S), threonine (T), valine (V), aspartic acid (D) and glutamic acid (E) at each position of the amino acid sequences of FRs of the reference antibodies are obtained. Here, the phrase "aligning the amino acid sequences of light chains of a plurality of reference antibodies" refers to aligning the amino acid sequences of light chains of a plurality of reference antibodies so that numbers of the amino acid residues in FR assigned by a predetermined numbering method match among the amino acid sequences of light chains of a plurality of reference antibodies. In the present embodiment, it is preferable to align the amino acid sequences of light chains of a plurality of reference antibodies so that the numbers of the amino acid residues in FR assigned by the Kabat method match. For each position, values of amino acid frequencies of R, S, T, V, D and E are summed to calculate total value. For example, in the aligned amino acid sequences of light chains of a plurality of reference antibodies, total value X (%) of amino acid frequencies at one position can be calculated from the numbers of R, S, T, V, D and E appearing at the position and the number of the obtained amino acid sequences of light chains of reference antibodies, by following formula (I). This calculation is performed for each position of the aligned amino acid sequences containing FR1 and/or FR3 of light chains of a plurality of reference antibodies. The number of the amino acid sequences of light chains of reference antibodies used in the calculation may differ from position to position. For example, the value of X in L1 may be calculated based on 10000 amino acid sequences of light chains of reference antibodies, and the value of X in L2 may be calculated based on 15000 amino acid sequences of light chains of reference antibodies.

[Expression 1]

$$X = \frac{(\text{Number of } R) + (\text{Number of } S) + (\text{Number of } T) + (\text{Number of } V) + (\text{Number of } D) + (\text{Number of } E)}{(\text{Number of amino acid sequence of light chain of reference antibody})} \times 100 \quad (I)$$

Positions where the obtained total value of amino acid frequencies is 35% or more and preferably 37% or more are specified in the aligned amino acid sequences of light chains of a plurality of reference antibodies. Then, as the amino acid residues satisfying the above condition (1), amino acid residues present at positions corresponding to the positions specified from the plurality of reference antibodies, in FR of a light chain of an unmodified antibody are specified. The amino acid residues may be specified, for example, by aligning the amino acid sequence of a light chain of an unmodified antibody with the amino acid sequences of light chains of a plurality of reference antibodies. When the amino acid sequences of light chains of a plurality of reference antibodies are aligned, for example, based on FR defined by the Kabat method, amino acid residues in which the numbers of the amino acid residues assigned by the Kabat method are the same as positions in the sequence of the reference antibody in which the total value of amino acid frequencies is 35% or more in the FR of an unmodified antibody are specified.

In the present embodiment, the amino acid residues satisfying the above condition (2) is specified based on the amino acid sequence of a light chain of an unmodified antibody. Specifically, first, three-dimensional structure data of a light chain of an unmodified antibody is obtained by using the amino acid sequence of a light chain of an unmodified antibody. The three-dimensional structure data includes coordinate data of each amino acid residue constituting the protein, and data capable of visualizing a three-dimensional structure of the protein by a known molecular graphics program such as RasMol or Jmol is preferable. The three-dimensional structure data may be obtained by performing known three-dimensional structure analysis such as X-ray crystal structure analysis and NMR analysis on the light chain of an unmodified antibody. In a preferred embodiment, the three-dimensional structure data is obtained by retrieving the amino acid sequence of a light chain of an unmodified antibody from a known protein three-dimensional structure database such as Protein Data Bank (PDB) or Biological Magnetic Resonance Bank (BMRB). When the database has a protein having a sequence matching the amino acid sequence of a light chain of an unmodified antibody, three-dimensional structure data of the protein is downloaded.

When there is no three-dimensional structure data of a light chain of an unmodified antibody in the protein three-dimensional structure database, information necessary for creating the three-dimensional structure data may be acquired, and three-dimensional structure data may be created based on the information. For example, three-dimensional structure data may be created by a homology modeling method or the like, based on the amino acid sequence of a light chain of an unmodified antibody. In the homology modeling method, as the information necessary for creating three-dimensional structure data, an amino acid sequence of a light chain of an antibody having at least 20% identity with the amino acid sequence of a light chain of an unmodified antibody and having a known three-dimensional structure (hereinafter, also referred to as "reference sequence") is used. In the art, it is known that proteins having high amino acid sequence identity are similar in three-dimensional structure to each other. The reference sequence can be obtained from a known database such as GenBank, abYsis, and IMGT. In the homology modeling method, the amino acid sequence of a light chain of an unmodified antibody and the reference sequence are aligned, and based on the result of the alignment, three-dimensional structure of a light chain of an unmodified antibody is constructed from a known structure of the reference sequence. The creation of three-dimensional structure data by the homology modeling method itself is known, and can be performed by a known three-dimensional structure prediction program such as MODELLER.

Next, based on the obtained three-dimensional structure data, a ratio of solvent-exposed surface area of each amino acid residue of FR of an unmodified antibody is obtained. In the art, the solvent-exposed surface area is defined as a locus surface of a center of a probe sphere (1.4 Å) when the probe sphere assuming a water molecule is rolled so as to be in contact with a surface (Van der Waals surface) of a protein molecule. The solvent-exposed surface area itself is a known index. The solvent-exposed surface area of a protein can be obtained from three-dimensional structure data of the protein by a known program or software such as SURFace, GETAREA, or Discovery Studio. It is also possible to obtain the solvent-exposed surface area of each amino acid residue in the protein. The solvent-exposed surface area of the amino acid residue in the protein depends on a size of side chain of the amino acid. Therefore, the ratio of solvent-exposed surface area is used as an index standardizing the solvent-exposed surface area of the amino acid residue in the protein by the size of side chain of the amino acid. The ratio of solvent-exposed surface area itself is a known index. For example, ratio of solvent-exposed surface area Y (%) of amino acid X in protein A is calculated by following formula (II). In the formula, "Ala-X-Ala" is a tripeptide consisting of a sequence in which the amino acid X is sandwiched between two alanines.

[Expression 2]

$$Y = \frac{\left(\text{Solvent-exposed surface area of amino acid } X \text{ in protein } A\right)}{\left(\text{Solvent-exposed surface area of amino acid } X \text{ in } Ala\text{-}X\text{-}Ala\right)} \times 100 \quad \text{(II)}$$

Then, in the amino acid sequence of FR of an unmodified antibody, amino acid residues having an obtained ratio of solvent-exposed surface area of 20% or more and preferably 25% or more are specified. As a result, in the amino acid sequence of FR of an unmodified antibody, amino acid residues present at positions where total value of amino acid frequencies of R, S, T, V, D and E is 35% or more and having a ratio of solvent-exposed surface area of 20% or more can be specified.

Among the amino acid residues satisfying the above conditions (1) and (2), the number of amino acid residues to be changed to charged amino acid residues is, for example, 3, 4, 5, 6, 7, 8, 9, 10, 11, 12, 13, 14, 15, 16, 17 or 18. The charged amino acid residues may be basic amino acid residues or acidic amino acid residues. Preferably, the charged amino acid residues are amino acid residues of the same charge. The charged amino acid residues may be the same residues or different residues. The basic amino acid residue refers to a lysine residue, an arginine residue, and a histidine residue. The acidic amino acid residue refers to an aspartic acid residue and a glutamic acid residue. In the present embodiment, as the charged amino acid residue, a basic amino acid residue is preferable, and a lysine residue and an arginine residue are particularly preferable.

Among the amino acid residues satisfying the above conditions (1) and (2), the amino acid residues to be changed to charged amino acid residues are preferably neutral amino acid residues. The neutral amino acid residue refers to an alanine residue, an asparagine residue, an isoleucine residue, a glycine residue, a glutamine residue, a cysteine residue, a threonine residue, a serine residue, a tyrosine residue, a phenylalanine residue, a proline residue, a valine residue, a methionine residue, a leucine residue, and a tryptophan residue.

When the amino acid residue satisfying the above conditions (1) and (2) is a charged amino acid residue, the amino acid residue may be left as it is. Alternatively, when the amino acid residue satisfying the above conditions (1) and (2) is an acidic amino acid residue, the amino acid residue may be changed to a basic amino acid residue. When the amino acid residue satisfying the above conditions (1) and (2) is a basic amino acid residue, the amino acid residue may be changed to an acidic amino acid residue.

In the present embodiment, when electrical characteristic of CDR based on the amino acid sequence of the CDR of the unmodified antibody is neutral, the amino acid residues satisfying the above conditions (1) and (2) may be changed to charged amino acid residues. The charged amino acid residues are preferably basic amino acid residues. Here, the electrical characteristic of CDR is an index uniquely defined by the present inventors. The electrical characteristic of CDR is determined based on the number of charged amino acid residues in the amino acid sequence of the CDR.

Specifically, the electrical characteristic of CDR is determined by following formula (III).

Z=[Number of basic amino acid residues in amino acid sequence of CDR]−[Number of acidic amino acid residues in amino acid sequence of CDR]   (III)

wherein when Z is −1, 0 or 1, the electrical characteristic of CDR is neutral,
when Z is 2 or more, the electrical characteristic of CDR is positively charged, and
when Z is −2 or less, the electrical characteristic of CDR is negatively charged.

The electrical characteristic of CDR may be determined based on the amino acid sequence of CDR of a light chain and/or a heavy chain. When determining the electrical characteristic of CDR of the light chain, the amino acid sequence of the CDR in the formula (III) refers to all amino acid sequences of CDR1, CDR2 and CDR3 of the light chain. When determining the electrical characteristic of CDR of the heavy chain, the amino acid sequence of the CDR in the formula (III) refers to all amino acid sequences of CDR1, CDR2 and CDR3 of the heavy chain. Preferably, it is determined based on the amino acid sequences of the CDRs of both the light chain and heavy chain. In this case, the amino acid sequence of the CDR in the formula (III) refers to all amino acid sequences of CDR1, CDR2 and CDR3 of the light chain and CDR1, CDR2 and CDR3 of the heavy chain. In the present embodiment, in an unmodified antibody whose electrical characteristic determined based on the amino acid sequences of the CDRs of both the light chain and the heavy chain is neutral, at least 3 of the amino acid residues satisfying the above conditions (1) and (2) may be changed to charged amino acid residues, and preferably basic amino acid residues.

The amino acid sequence of the CDR can be obtained from a public database that discloses the sequence of the antibody gene. Alternatively, when there is a hybridoma that produces an unmodified antibody, the amino acid sequence of the CDR can be obtained by obtaining a nucleic acid encoding a heavy chain and a light chain from the hybridoma by a known method, and sequencing the base sequence of the nucleic acid.

The electrical characteristic of CDR differs depending on the antibody. For example, in the Kabat method, CDR of a light chain of a wild-type (i.e., unmodified) anti-lysozyme antibody used in the examples described later has one basic amino acid residue (arginine) and has no acidic amino acid residue. CDR of a heavy chain has one basic amino acid residue (lysine) and three acidic amino acid residues (aspartic acid). Thus, the electrical characteristic of CDR of the wild-type anti-lysozyme antibody is defined as neutral (Z=−1). The electrical characteristic of CDR of the anti-lysozyme antibody based on Chothia method is negatively charged.

The amino acid residue satisfying the above conditions (1) and (2) is preferably an amino acid residue present in FR1 and/or FR3. Examples of the amino acid residue satisfying the above conditions (1) and (2) in FR1 and FR3 of the light chain include 1st, 3rd, 5th, 7th, 9th, 10th, 12th, 14th, 17th, 18th, 20th, 22nd, 60th, 63rd, 65th, 67th, 69th, 70th, 72nd, 74th, 76th, 77th, 79th and 81st amino acid residues of the light chain defined by the Kabat method. Among them, the 1st, 3rd, 5th, 7th, 9th, 10th, 12th, 14th, 17th, 18th, 20th and 22nd amino acid residues are present in FR1 of the light chain defined by the Kabat method, and the 60th, 63rd, 65th, 67th, 69th, 70th, 72nd, 74th, 76th, 77th, 79th and 81st amino acid residues are present in FR3 of the light chain defined by the Kabat method.

In a preferred embodiment, the amino acid residue satisfying the above conditions (1) and (2) are the 3rd, 5th, 9th, 17th, 18th, 20th, 22nd, 60th, 63rd, 65th, 67th, 70th, 72nd, 74th, 76th, 77th, 79th and 81st amino acid residues of the light chain defined by the Kabat method. Among these amino acid residues, at least 3 amino acid residues to be changed to charged amino acid residues preferably contain at least one selected from the 3rd, 5th, 9th, 17th, 18th, 20th, 22nd, 60th, 74th, 76th, 77th, 79th and 81st amino acid residues of the light chain defined by the Kabat method. More preferably, at least 3 amino acid residues to be changed to charged amino acid residues preferably contain at least 3 selected from the 3rd, 5th, 9th, 17th, 18th, 20th, 22nd, 60th, 74th, 76th, 77th, 79th and 81st amino acid residues of the light chain defined by the Kabat method.

When modifying amino acid residues of FR1 of a light chain of an unmodified antibody, at least 3 amino acid residues to be changed to charged amino acid residues are preferably selected from the 3rd, 5th, 9th, 17th, 18th, 20th and 22nd amino acid residues of the light chain defined by the Kabat method. Examples of the 3 amino acid residues include any combination of following 1) to 4).
1) 3rd, 5th and 9th Amino acid residues of the light chain defined by the Kabat method;
2) 17th, 18th and 20th Amino acid residues of the light chain defined by the Kabat method;
3) 18th, 20th and 22nd Amino acid residues of the light chain defined by the Kabat method; and
4) 5th, 9th and 22nd Amino acid residues of the light chain defined by the Kabat method.

When modifying amino acid residues of FR3 of a light chain of an unmodified antibody, at least 3 amino acid residues to be changed to charged amino acid residues are preferably selected from the 60th, 63rd, 65th, 67th, 70th, 72nd, 74th, 76th, 77th, 79th and 81st amino acid residues of the light chain defined by the Kabat method. Among these amino acid residues, at least 3 amino acid residues to be changed to charged amino acid residues preferably contain at least one selected from 60th, 74th, 76th, 77th, 79th and 81st amino acid residues of the light chain defined by the Kabat method. More preferably, at least 3 amino acid residues to be changed to charged amino acid residues preferably contain at least 3 selected from the 60th, 74th, 76th, 77th, 79th and 81st amino acid residues of the light chain defined by the Kabat method. Examples of the 3 amino acid residues include any combination of following 5) to 8).
5) 60th, 76th and 77th Amino acid residues of the light chain defined by the Kabat method;
6) 74th, 76th and 77th Amino acid residues of the light chain defined by the Kabat method;
7) 77th, 79th and 81st Amino acid residues of the light chain defined by the Kabat method; and
8) 76th, 77th and 81st Amino acid residues of the light chain defined by the Kabat method.

Examples of the method of changing the amino acid residue satisfying the above conditions (1) and (2) to a charged amino acid residue include substitution, insertion and the like of the amino acid residue. In the modification by inserting an amino acid residue, a charged amino acid residue is inserted between the amino acid residue satisfying the above conditions (1) and (2) and an amino acid residue adjacent to the N-terminal side of the amino acid residue. For example, by inserting a charged amino acid residue between L2 amino acid residue and L3 amino acid residue of the unmodified antibody, the L3 amino acid residue can be changed to a charged amino acid residue. In a preferred embodiment, the amino acid residue satisfying the above conditions (1) and (2) is substituted with a charged amino acid residue.

In the present embodiment, the amino acid residue of FR of an unmodified antibody can be changed to a charged amino acid residue by known methods such as DNA recombination technology and other molecular biological techniques. For example, when there is a hybridoma that produces an unmodified antibody, RNA extracted from the hybridoma is used to synthesize a polynucleotide encoding the light chain, by a reverse transcription reaction and a rapid amplification of cDNA ends (RACE) method. This polynucleotide is amplified by PCR using a primer for modifying at least 3 amino acid residues of FR to obtain a polynucleotide encoding a light chain in which FR has been modified. The obtained polynucleotide is incorporated into an expression vector known in the art to obtain an expression vector containing a polynucleotide encoding a modified antibody. The type of the expression vector is not particularly limited, and it may be an expression vector for mammalian cells or an expression vector for *E. coli*. By transforming or transfecting the obtained expression vector into an appropriate host cell (for example, mammalian cell or *E. coli*), an antibody with improved affinity can be obtained.

When obtaining a modified antibody which is a single chain antibody (scFv), as shown in, for example, PCT International Application Publication No. 2013/084371 A1, RNA extracted from the hybridoma may be used to synthesize a polynucleotide encoding a light chain variable region by a reverse transcription reaction and PCR. This polynucleotide is ligated by overlap extension PCR or the like to obtain a polynucleotide encoding an unmodified scFv. The obtained polynucleotide is amplified by PCR using a primer for modifying at least 3 amino acid residues of FR to obtain a polynucleotide encoding scFv in which FR has been modified. The obtained polynucleotide is incorporated into an expression vector known in the art to obtain an expression vector containing a polynucleotide encoding a modified antibody in the form of scFv. By transforming or transfecting the obtained expression vector into an appropriate host cell, a modified antibody in the form of scFv can be obtained.

When there is no hybridoma that produces an unmodified antibody, an antibody-producing hybridoma may be prepared by known methods such as those described in, for example, Kohler and Milstein, Nature, vol. 256, p. 495-497, 1975. Alternatively, RNA obtained from the spleen of an animal such as a mouse immunized with an antigen of interest may be used. When using the RNA obtained from the spleen, for example, as shown in Fukunaga A and Tsumoto K, Protein Eng. Des. Sel. 2013, vol. 26, pp. 773-780, a polynucleotide encoding an unmodified scFv having a desired affinity may be selected by a phage display method or the like, from the obtained polynucleotides encoding an unmodified scFv.

2. Antibody with Improved Affinity and Production Method Thereof

An antibody with improved affinity for an antigen as compared to an unmodified antibody of the present embodiment (hereinafter, also referred to as "antibody with improved affinity") is characterized in that, in an amino acid sequence of FR of a light chain of an unmodified antibody, at least 3 of amino acid residues present at positions where total value of amino acid frequencies of R, S, T, V, D and E is 35% or more and having a ratio of solvent-exposed surface area of 20% or more are changed to charged amino acid residues. The antibody with improved affinity is the same as the "modified antibody" described in the description of the method for improving affinity of the present embodiment.

The antibody with improved affinity of the present embodiment is preferably an antibody in which the amino acid residues of FR1 and/or FR3 of a light chain of an unmodified antibody are changed to charged amino acid residues. Examples of the antibodies include antibodies in which at least 3 of the 1st, 3rd, 5th, 7th, 9th, 10th, 12th, 14th, 17th, 18th, 20th, 22nd, 60th, 63rd, 65th, 67th, 69th, 70th, 72nd, 74th, 76th, 77th, 79th and 81st amino acid residues of the light chain defined by the Kabat method in the unmodified antibody are changed to charged amino acid residues. In a preferred embodiment, the antibody with improved affinity is an antibody in which at least 3 amino acid residues selected from the 3rd, 5th, 9th, 17th, 18th, 20th, 22nd, 60th, 63rd, 65th, 67th, 70th, 72nd, 74th, 76th, 77th, 79th and 81st amino acid residues of the light chain defined by the Kabat method in the unmodified antibody are changed to charged amino acid residues. In this antibody, the above 3 amino acid residues more preferably contain at least one selected from the 3rd, 5th, 9th, 17th, 18th, 20th, 22nd, 60th, 74th, 76th, 77th, 79th and 81st amino acid residues of the light chain defined by the Kabat method. The charged amino acid residues are preferably basic amino acid residues.

When the antibody with improved affinity of the present embodiment is an antibody in which the amino acid residue of FR1 of a light chain of an unmodified antibody is modified, an antibody in which at least 3 of the 3rd, 5th, 9th, 17th, 18th, 20th and 22nd amino acid residues of the light chain defined by the Kabat method in the unmodified antibody are changed to charged amino acid residues is preferable. Examples of the at least 3 amino acid residues include any combination of the above 1) to 4).

When the antibody with improved affinity of the present embodiment is an antibody in which the amino acid residue of FR1 of a light chain of an unmodified antibody is modified, an antibody in which at least 3 of the 60th, 63rd, 65th, 67th, 70th, 72nd, 74th, 76th, 77th, 79th and 81st amino acid residues of the light chain defined by the Kabat method in the unmodified antibody are changed to charged amino acid residues is preferable. In particular, an antibody in which at least 3 selected from the 60th, 74th, 76th, 77th, 79th and 81st amino acid residues of the light chain defined by the Kabat method are changed to charged amino acid residues is preferable. Examples of the at least 3 amino acid residues include any combination of the above 5) to 8).

The antibody with improved affinity of the present embodiment can be obtained by a method for producing an antibody with improved affinity for an antigen as compared to an unmodified antibody of the present embodiment (hereinafter, also referred to as "production method"). In the production method of the present embodiment, first, in the amino acid sequence of FR of a light chain of an antibody (unmodified antibody), at least 3 of amino acid residues present at positions where total value of amino acid frequencies of R, S, T, V, D and E is 35% or more and having a ratio of solvent-exposed surface area of 20% or more are changed to charged amino acid residues. Modifying the amino acid residue in the unmodified antibody is the same as that described for the method for improving affinity of the present embodiment.

Subsequently, the antibody obtained by the above modification is recovered. For example, a host cell expressing an antibody with improved affinity is dissolved in a solution containing an appropriate solubilizer to liberate the antibody in the solution. When the above host cell secretes an antibody into the medium, the culture supernatant is recovered. The liberated antibody can be recovered by methods known in the art such as affinity chromatography. For example, when the produced antibody is IgG, the antibody can be recovered by affinity chromatography using protein A or G. If necessary, the recovered antibody may be purified by methods known in the art such as gel filtration.

3. Method for Analyzing Amino Acid Sequence of Antibody

The scope of the present disclosure also includes a method for analyzing an amino acid sequence of an antibody (hereinafter, also referred to as "analysis method"). In the analysis method of the present embodiment, total value of amino acid frequencies of R, S, T, V, D and E at each position in the amino acid sequence of FR of a light chain of an antibody and a ratio of solvent-exposed surface area of each amino acid residue in the amino acid sequence are obtained, and the obtained total value of amino acid frequencies at each position and ratio of solvent-exposed surface area of each amino acid residue are output. The output information is useful for examining candidates for amino acid residues to be modified, for example, when modifying the analyzed antibody. Details of the total value of amino acid frequencies and the ratio of solvent-exposed surface area are the same as those described for the method for improving affinity of the present embodiment. The analysis method of the present embodiment may be performed using, for example, an amino acid sequence analysis system as shown in FIG. 1.

Overview of Amino Acid Sequence Analysis System

An example of the amino acid sequence analysis system will be described below with reference to the drawings. However, the present embodiment is not limited only to the embodiment shown in this example. With reference to FIG. 1, the amino acid sequence analysis system includes an analysis device 10 of amino acid sequence and a sequence data server 20. The analysis device 10 and the sequence data server 20 are connected to each other via a network 30 such as an intranet or an internet. In FIG. 1, the analysis device 10 is shown as a general-purpose computer system including a control unit 100 (computer main body), an input unit 101, and a display unit 102, but the analysis device 10 is not limited to this form.

When sequence information such as amino acid sequences of light chains of a plurality of reference antibodies and three-dimensional structure data of a light chain of an antibody is requested from the analysis device 10 to the sequence data server 20 via the network 30, the sequence information is downloaded from the sequence data server 20 to the analysis device 10. The sequence data server 20 includes a database in which information on amino acid sequences such as information on the amino acid sequences of light chains of a plurality of reference antibodies and the three-dimensional structure data of a light chain of an antibody are stored (hereinafter, also referred to as "amino acid sequence database"). The sequence data server 20 may be an external data server managed by a third party different from a user who uses the analysis device 10. Examples of the database that can be used from the external data server (hereinafter, also referred to as "external database") include GenBank, abYsis, IMGT, PDB, BMRB, and the like.

Although one sequence data server is shown in FIG. 1, the analysis device 10 may be connected to a plurality of sequence data servers. The plurality of sequence data servers may include respectively different types of amino acid sequence databases. For example, one sequence data server may include a database of amino acid sequence information for a protein, including the amino acid sequences of light chains of a plurality of reference antibodies, and another sequence data server may include a database of three-dimensional structure data of the protein including the light chain of an antibody.

The analysis device 10 obtains an amino acid sequence of a light chain of an unmodified antibody from an input by the user or a storage medium 40 described later. The analysis device 10 requests the sequence data server 20 via the network 30 for the amino acid sequences of light chains of a plurality of reference antibodies and the three-dimensional structure data of a light chain of an antibody. The sequence data server 20 provides the requested data to the analysis device 10 via the network 30. Then, the analysis device 10 analyzes the amino acid sequence of the unmodified antibody using the obtained sequence.

Hardware Configuration of Amino Acid Sequence Analysis System

Figure 2:
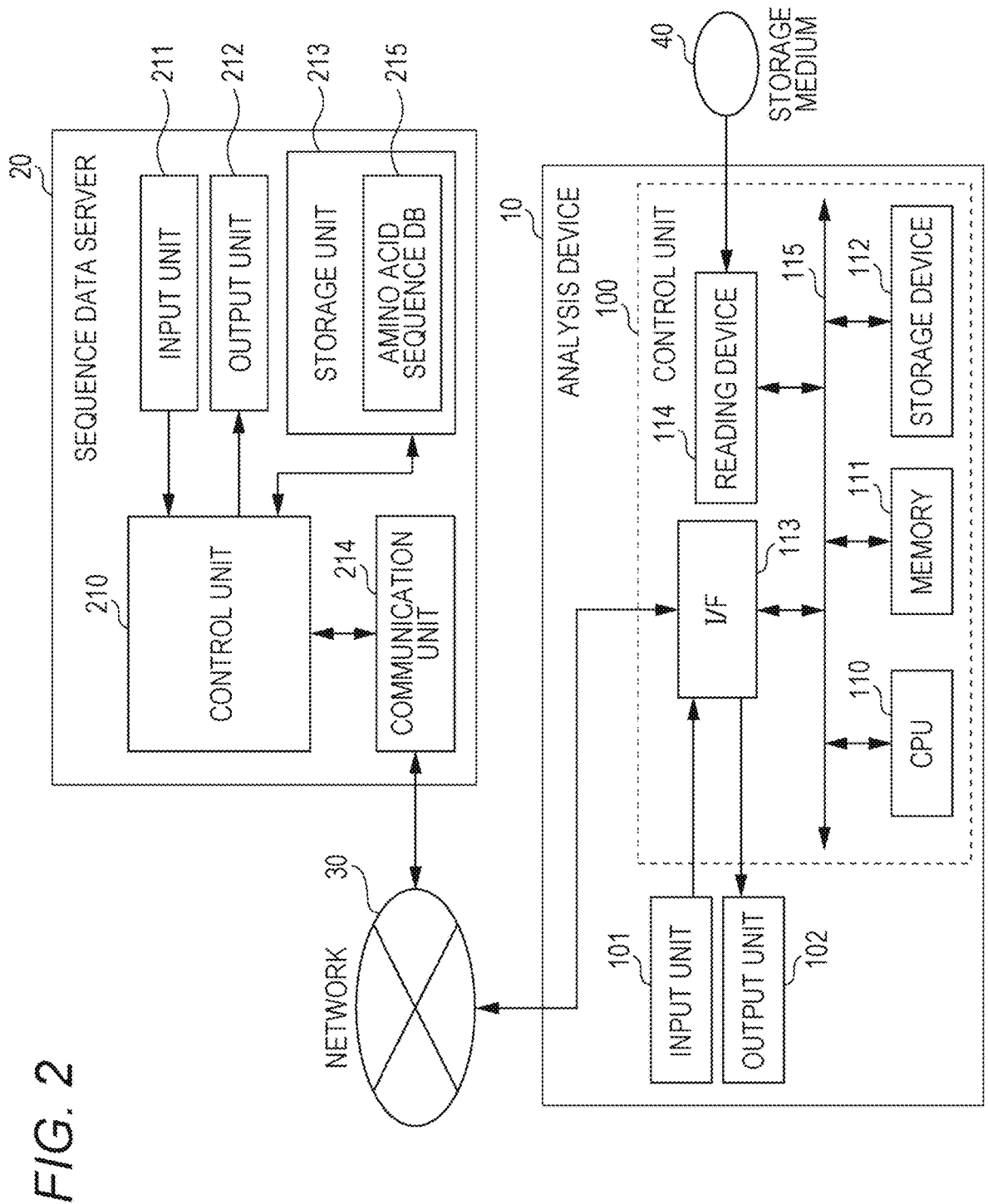
FIG. 2 is a diagram showing a hardware configuration of an amino acid sequence analysis system.

With reference to FIG. 2, the control unit 100 of the analysis device 10 includes Central Processing Unit (CPU) 110, memory 111, a storage device 112, an interface 113, a reading device 114, and a bus 115 for data-communicably connecting them. The control unit 100 is communicably connected to external devices such as the input unit 101 and the output unit 102 and the network 30 via the interface 113. The storage medium 40 is a computer-readable, non-transitory tangible storage medium such as a CD-ROM or a USB memory. The sequence data server 20 includes a control unit 210, an input unit 211, an output unit 212, a storage unit 213, and a communication unit 214. Amino acid sequence database 215 is stored in the storage unit 213. The sequence data server 20 is communicably connected to the network 30 via the communication unit 214. The input units 101 and 211 are input devices such as a mouse and a keyboard. The output units 102 and 212 are display devices such as a liquid crystal display.

The CPU 110 executes a computer program of the present embodiment stored in the memory 111 or the storage device 112 to perform a process described later. The memory 111 includes Read Only Memory (ROM) and Random Access Memory (RAM). The ROM includes, for example, mask ROM, PROM, EPROM, EEPROM, and the like. In the ROM, a computer program executed by the CPU 110 and data used for executing the computer program are recorded. The RAM includes, for example, SRAM, DRAM, and the like. The RAM is used for reading the program recorded in the ROM and the storage device 112. The RAM is used as a work area of the CPU 110 when these programs are executed.

The storage device 112 includes, for example, a hard disk. In the storage device 112, programs such as operating systems and application programs for execution by the CPU 110, and data used for executing the programs are stored. Examples of the application program include the computer program of the present embodiment, a program for executing amino acid sequence alignment, a program for executing amino acid frequency calculation, a program for executing calculation of ratio of solvent-exposed surface area, and the like. Further, in the storage device 112, respective threshold values of the amino acid frequency and the ratio of solvent-exposed surface area may be recorded.

The reading device 114 includes a CD-ROM drive, a DVD-ROM drive, a USB port, an SD card reader, a CF card reader, a memory stick reader, a solid state drive, a flexible disk drive, and the like. The reading device 114 can read data recorded on the storage medium 40 (e.g., information on the amino acid sequences of light chains of an unmodified antibody and/or a plurality of reference antibodies and/or the nucleic acid sequence encoding them, and the like), and a computer program.

Process Procedure of Analysis Device of Amino Acid Sequence

Figure 3:
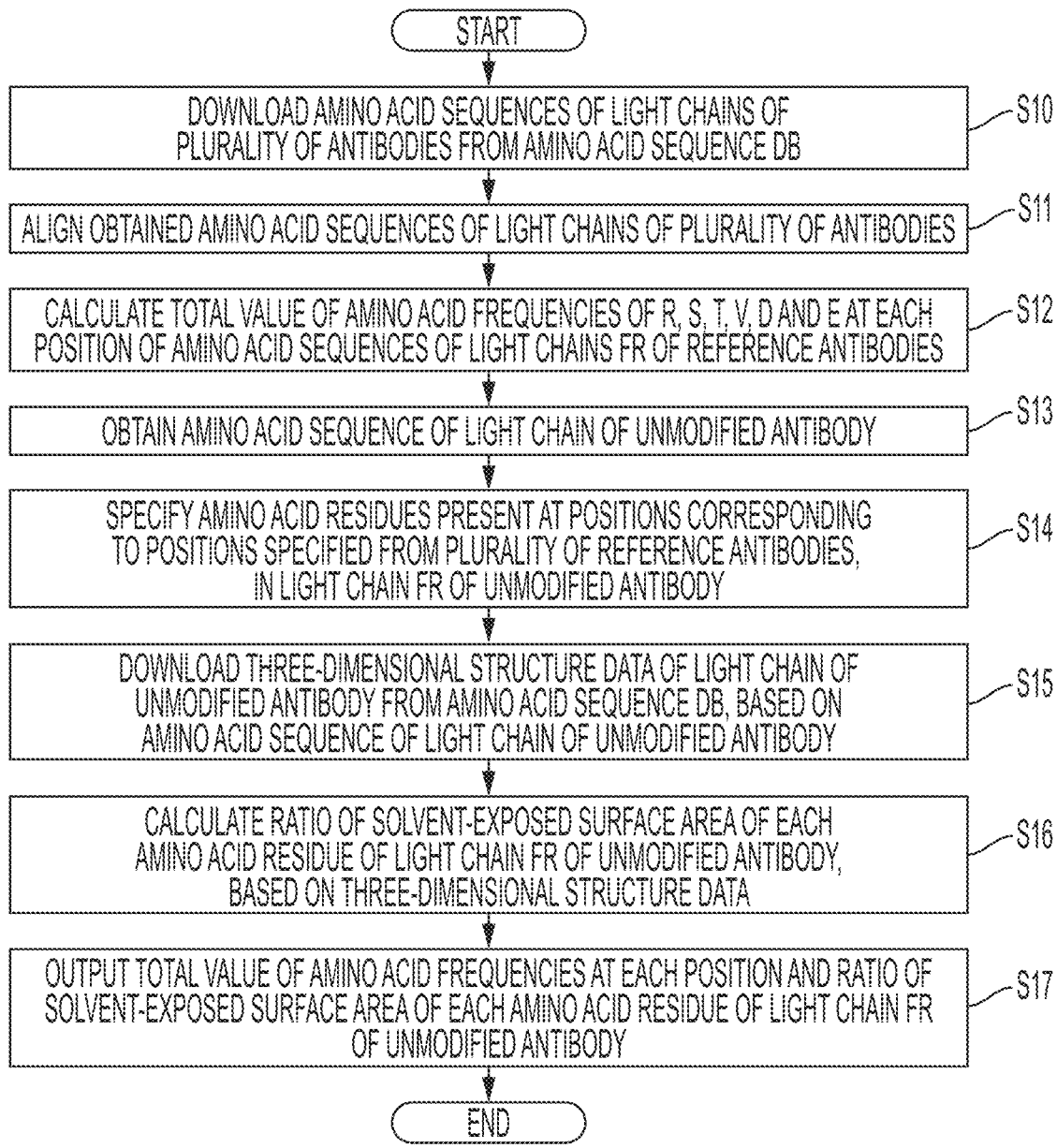
FIG. 3 is a flowchart showing an analysis process of amino acid sequence of an unmodified antibody by an analysis device of amino acid sequence.

With reference to FIG. 3, an analysis process of amino acid sequence of an antibody executed by the analysis device 10 will be described. Here, using the amino acid sequences of light chains of a plurality of reference antibodies and the three-dimensional structure data of a light chain of an unmodified antibody downloaded from an external database, a case of outputting total value of amino acid frequencies at each position and a ratio of solvent-exposed surface area of each amino acid residue will be described as an example. However, the present embodiment is not limited only to this example. Unless otherwise specified in the following description, the process performed by the control unit 100 means the process performed by the CPU 110.

In step S10, the control unit 100 downloads data of the amino acid sequences of light chains of a plurality of reference antibodies from the amino acid sequence database 215 of the sequence data server 20 via the network 30, and the control unit 100 stores the data in the storage device 112. The amino acid sequence to be downloaded may be a sequence of the entire light chain or a sequence of a part of the light chain containing an amino acid sequence of FR1 and/or FR3. When the user already has the data of the amino acid sequences of light chains of a plurality of reference antibodies, the control unit 100 may obtain the data of the amino acid sequences input by the user instead of downloading. The input may be performed by the input unit 101, or the input may be performed by transferring the data of the amino acid sequences stored in the storage medium 40 to the storage device 112.

In step S11, the control unit 100 aligns the obtained amino acid sequences of light chains of a plurality of reference antibodies. Specifically, the control unit 100 aligns the amino acid sequences of a plurality of reference antibodies so that the numbers of the amino acid residues in FR assigned by the Kabat method match. Alignment may be performed based on a numbering method other than the Kabat method. In step S12, the control unit 100 calculates total value of amino acid frequencies of R, S, T, V, D and E at each position of the amino acid sequences of FRs of a plurality of reference antibodies. This calculation is the same as that described for the method for improving affinity of the present embodiment.

In step S13, the control unit 100 obtains an amino acid sequence of a light chain of an unmodified antibody. The amino acid sequence of a light chain of an unmodified antibody to be obtained may be an amino acid sequence of the entire light chain or an amino acid sequence of a part of the light chain. The amino acid sequence of a part of the light chain preferably contains an amino acid sequence of FR1 and/or FR3, and more preferably further contains an amino acid sequence of CDR. In a preferred embodiment, the control unit 100 obtains the amino acid sequence of the entire light chain of an unmodified antibody. The amino acid sequence may be input by the user, or the amino acid sequence may be previously stored in the storage medium 40 or the storage device 112. When the amino acid sequence of a light chain of an unmodified antibody is present in the amino acid sequence database 215, the control unit 100 may download the data of the amino acid sequence. In step S14, the control unit 100 specifies amino acid residues present at positions corresponding to the positions specified from the plurality of reference antibodies in FR of an unmodified antibody are specified. The control unit 100 may specify the amino acid residues by aligning the amino acid sequence of a light chain of an unmodified antibody with the amino acid sequences of light chains of a plurality of reference antibodies. As a result, the control unit 100 obtains the calculated total value of amino acid frequencies as total value of amino acid frequencies at each position of the amino acid sequence of FR of an unmodified antibody, and the control unit 100 stores the total value in the storage device 112.

In step S15, the control unit 100 downloads three-dimensional structure data of a light chain of an unmodified antibody from the amino acid sequence database 215, based on the amino acid sequence of a light chain of an unmodified antibody. The control unit 100 retrieves the amino acid sequence of a light chain of an unmodified antibody from the amino acid sequence database 215. When the database contains a protein having a sequence matching the amino acid sequence of a light chain of an unmodified antibody, the control unit 100 downloads three-dimensional structure data of the protein, and the control unit 100 stores the data in the storage device 112 as the three-dimensional structure data of a light chain of an unmodified antibody.

In step S16, the control unit 100 calculates a ratio of solvent-exposed surface area of each amino acid residue of FR of an unmodified antibody, based on the obtained three-dimensional structure data, and the control unit 100 stores the ratio in the storage device 112. This calculation is the same as that described for the method for improving affinity of the present embodiment. When the user has the three-dimensional structure data of a light chain of an unmodified antibody, the control unit 100 may obtain the three-dimensional structure data input by the user instead of downloading. The input may be performed by the input unit 101, or the input may be performed by transferring the three-dimensional structure data stored in the storage medium 40 to the storage device 112. When there is no three-dimensional structure data of a light chain of an unmodified antibody in the amino acid sequence database 215, the control unit 100 may acquire information necessary for creating the three-dimensional structure data from the database, and the control unit 100 may create three-dimensional structure data based on the information. Specifically, the control unit 100 retrieves for a reference sequence from the amino acid sequence database 215, and the control unit 100 downloads its amino acid sequence. Subsequently, the control unit 100 aligns the reference sequence with the amino acid sequence of the unmodified antibody. Then, the control unit 100 creates three-dimensional structure data of a light chain of an unmodified antibody from a known structure of the reference sequence based on the alignment result. The creation of the three-dimensional structure data is the same as that described for the method for improving affinity of the present embodiment.

In step S17, the control unit 100 transmits the total value of amino acid frequencies at each position of the amino acid sequence of FR of an unmodified antibody specified in step S14, and the ratio of solvent-exposed surface area of each amino acid residue of FR of an unmodified antibody calculated in step S16 to the output unit 102. FIG. 4 shows an example of a screen of analysis results displayed on the output unit 102. This screen shows the total value of amino acid frequencies and the ratio of solvent-exposed surface area at each position (L1 to L23) of the amino acid sequence of FR1 of an unmodified antibody. However, the display of the screen is not limited to this example.

In the process shown in FIG. 3, step S13 may be performed before step S10, S11 or S12. Steps S15 and S16 may be performed before step S10, S11 or S12 as long as it is after the step of obtaining the amino acid sequence of the unmodified antibody (step S13). Steps S10 and S15 may be performed at the same time as long as it is after the step of obtaining the amino acid sequence of the unmodified antibody (step S13).

4. Method for Specifying Candidates for Antibody Modification Sites

The scope of the present disclosure also includes a method for specifying candidates for antibody modification sites (hereinafter, also referred to as a "specification method"). In the specification method of the present embodiment, total value of amino acid frequencies of R, S, T, V, D and E at each position in the amino acid sequence of FR of a light chain of an antibody and a ratio of solvent-exposed surface area of each amino acid residue in the amino acid sequence are obtained, and an amino acid residue present at positions where total value of amino acid frequencies is 35% or more and having a ratio of solvent-exposed surface area of 20% or more are changed to charged amino acid residues is specified as candidates for a site to be modified to improve affinity. Details of the total value of amino acid frequencies and the ratio of solvent-exposed surface area are the same as those described for the method for improving affinity of the present embodiment.

In the amino acid sequence of a light chain of an antibody, at least 3 of the amino acid residues specified by the specification method of the present embodiment are changed to charged amino acid residues, so that affinity of the antibody for an antigen can be improved as compared to that of the unmodified antibody. Then, by recovering the antibody in which the amino acid residue is modified, a modified antibody with improved affinity of the antibody for an antigen can be obtained. The modification of amino acid residue and the recovery of antibody are the same as those described for the method for improving affinity of the present embodiment and the production method of the present embodiment.

The specification method of the present embodiment can be performed by an amino acid sequence analysis system as shown in FIG. 1, similarly to the analysis method of the present embodiment. Outline and hardware configuration of the amino acid sequence analysis system for performing the specification method of the present embodiment are the same as those described for the analysis method of the present embodiment.

Process Procedure of Analysis Device of Amino Acid Sequence

Figure 5:
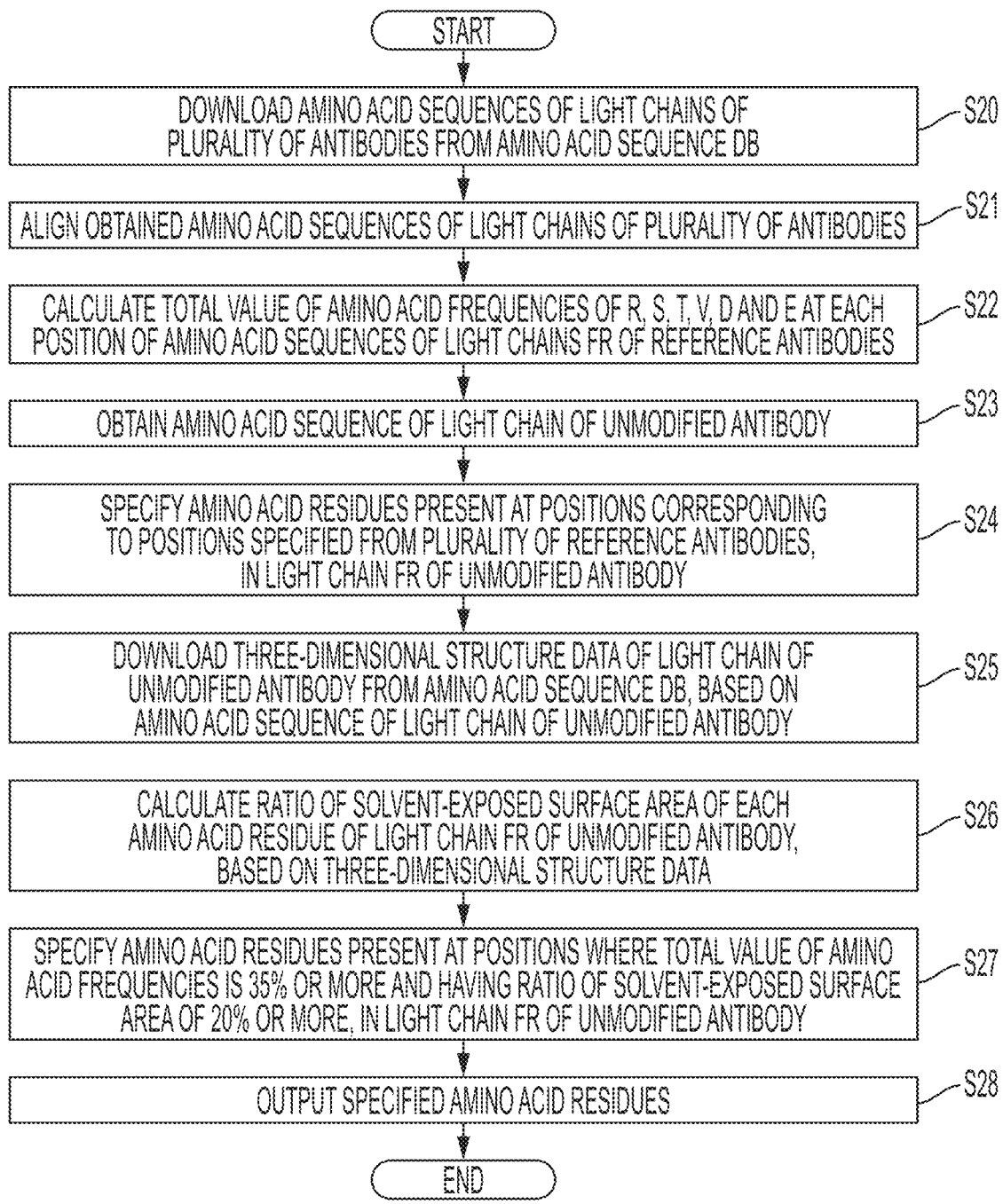
FIG. 5 is a flowchart showing an analysis process of amino acid sequence for specifying candidates for antibody modification sites by the analysis device of amino acid sequence.

With reference to FIG. 5, an analysis process of amino acid sequence for specifying candidates for antibody modification sites executed by the analysis device 10 will be described. Here, using the amino acid sequences of light chains of a plurality of reference antibodies and the three-dimensional structure data of a light chain of an unmodified antibody downloaded from an external database, a case of calculating total value of amino acid frequencies at each position and a ratio of solvent-exposed surface area of each amino acid residue will be described as an example. However, the present embodiment is not limited only to this example. Unless otherwise specified in the following description, the process performed by the control unit 100 means the process performed by the CPU 110. Details of steps S20 to S26 are the same as those described for steps S10 to S16.

In step S27, the control unit 100 specifies amino acid residues present at positions where total value of amino acid frequencies of R, S, T, V, D and E, among positions of the amino acid sequence of FR of an unmodified antibody specified in step S24, is 35% or more, and having a ratio of solvent-exposed surface area calculated in step S26 of 20% or more. Then, in step S28, the control unit 100 transmits the amino acid residues specified in step S27 to the output unit 102. FIG. 6 shows an example of a screen of analysis results displayed on the output unit 102. This screen shows the total value of amino acid frequencies and the ratio of solvent-exposed surface area at each position (L1 to L23) of the amino acid sequence of FR1 of a light chain of an unmodified antibody. In this screen, the positions and values of the amino acid residues specified in step S27 are highlighted in bold and markers. However, the display of the screen is not limited to this example. The specified amino acid residues are presented to the user as candidates for modification sites in the unmodified antibody.

Figure 7:
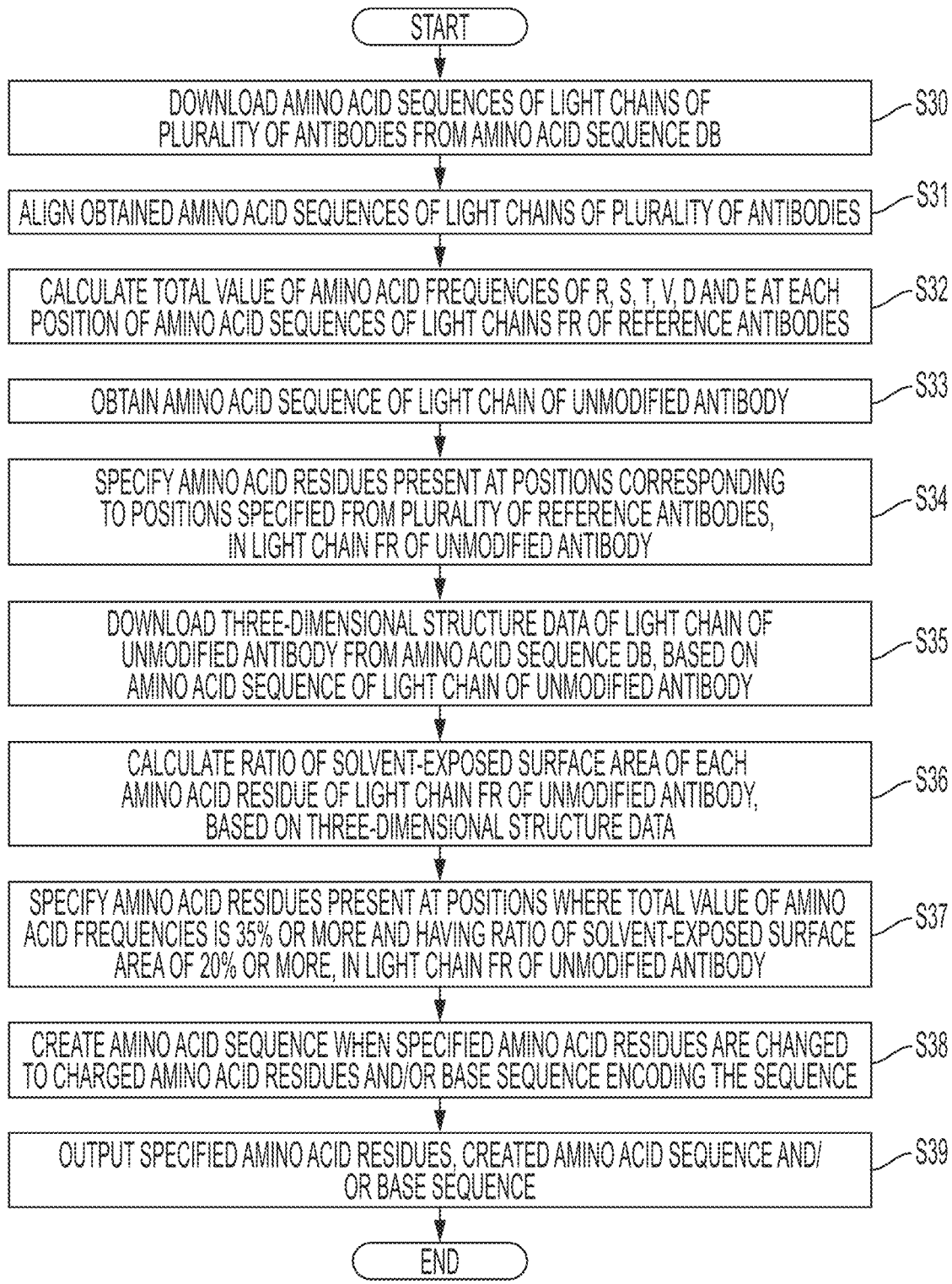
FIG. 7 is a flowchart showing an analysis process of amino acid sequence for creating a sequence when candidates for antibody modification sites are changed to charged amino acid residues by the analysis device of amino acid sequence.

With reference to FIG. 7, an analysis process of amino acid sequence for creating a sequence when the candidates for antibody modification sites are changed to charged amino acid residues executed by the analysis device 10 will be described. Here, using the amino acid sequences of light chains of a plurality of reference antibodies and the three-dimensional structure data of a light chain of an unmodified antibody downloaded from an external database, a case of calculating total value of amino acid frequencies at each position and a ratio of solvent-exposed surface area of each amino acid residue will be described as an example. However, the present embodiment is not limited only to this example. Unless otherwise specified in the following description, the process performed by the control unit 100 means the process performed by the CPU 110. Steps S30 to S36 are the same as described for steps S10 to S16, and step S37 is the same as step S27.

In step S38, the control unit 100 creates an amino acid sequence and/or a base sequence encoding the sequence when at least 3 of the amino acid residues specified in step S37 are changed to charged amino acid residues. When creating the amino acid sequence, the control unit 100 creates an amino acid sequence in which at least 3 of the amino acid residues specified in step S37 are changed to R, K, D or E (amino acid sequence of a light chain of a modified antibody), in the amino acid sequence of a light chain of an unmodified antibody obtained in step S33, and the control unit 100 stores the amino acid sequence in the storage device 112. Which amino acid residue is changed to the charged amino acid residue may be preset or may be determined by the user. Which of R, K, D and E is selected as the charged amino acid residue may be preset or may be determined by the user.

When creating a base sequence encoding the amino acid sequence of a light chain of a modified antibody, the control unit 100 creates an amino acid sequence in which at least 3 of the amino acid residues specified in step S37 are changed to R, K, D or E, in the amino acid sequence obtained in step S33, the control unit 100 converts it into a base sequence, and the control unit 100 stores the base sequence in the storage device 112. When there are a plurality of codons for one amino acid, which codon is selected may be preset or may be determined by the user. When creating a base sequence, the control unit 100 may obtain a base sequence encoding the light chain of an unmodified antibody in step S33. When the nucleotide sequence is obtained, the control unit 100 may create a base sequence encoding the amino acid sequence of a light chain of a modified antibody, by changing codons corresponding to the amino acid residues specified in step S37 to codons corresponding to the charged amino acid residues. Then, in step S39, the control unit 100 transmits the amino acid residues specified in step S37, the amino acid sequence of a light chain of a modified antibody and/or the base sequence encoding the amino acid sequence created in step S38 to the output unit 102.

In the specification method of the present embodiment, the electrical characteristic of CDR based on the amino acid sequence of the CDR of the unmodified antibody may be calculated and output. The electrical characteristic of CDR is the same as that described for the method for improving affinity of the present embodiment. When the calculated electrical characteristic of CDR is neutral, a modified amino acid sequence when at least 3 of the amino acid residues specified as candidates for modification sites are changed to charged amino acid residues (preferably basic amino acid residues) may be created, and the modified amino acid sequence may be output.

Figure 8:
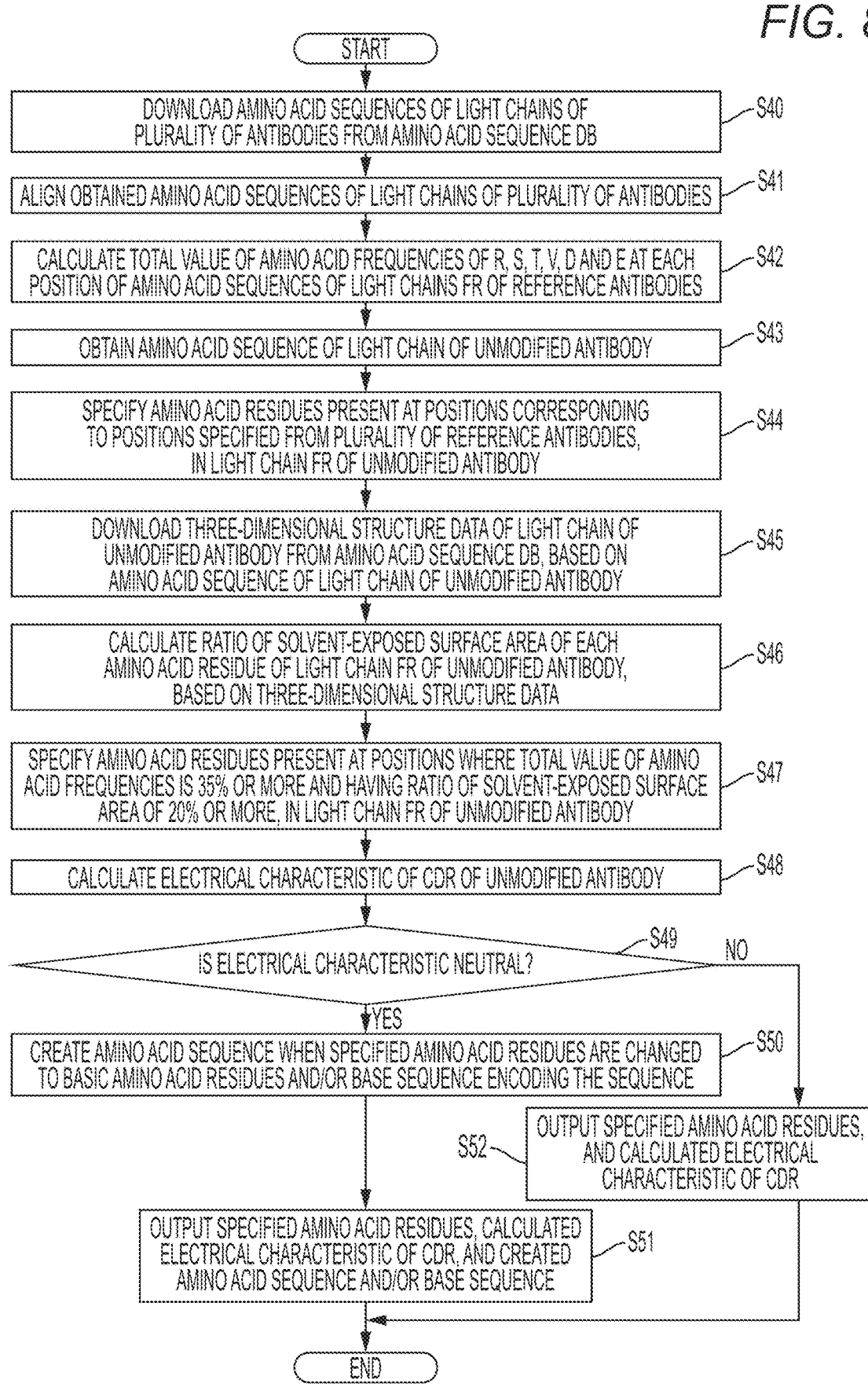
FIG. 8 is a flowchart showing an analysis process of amino acid sequence for creating a sequence when candidates for antibody modification sites are changed to basic amino acid residues when electrical characteristic of CDR is neutral by the analysis device of amino acid sequence.

With reference to FIG. 8, an analysis process of amino acid sequence for creating a sequence when candidates for antibody modification sites are changed to basic amino acid residues when the electrical characteristic of CDR is neutral executed by the analysis device 10 will be described. Here, using the amino acid sequences of light chains of a plurality of reference antibodies and the three-dimensional structure data of a light chain of an unmodified antibody downloaded from an external database, a case of calculating total value of amino acid frequencies at each position and a ratio of solvent-exposed surface area of each amino acid residue will be described as an example. However, the present embodiment is not limited only to this example. Unless otherwise specified in the following description, the process performed by the control unit 100 means the process performed by the CPU 110. Steps S40 to S46 are the same as described for steps S10 to S16, and step S47 is the same as step S27.

In step S48, the control unit 100 calculates the electrical characteristic of CDR of the unmodified antibody, based on the amino acid sequence of a light chain of an unmodified antibody obtained in step S43. The electrical characteristic of CDR is calculated by the above formula (III). In step S49, whether or not the calculated electrical characteristic of CDR is neutral is determined. When the value calculated by the above formula (III) is −1, 0 or 1, the electrical characteristic of CDR is determined to be neutral, and the process proceeds to step S50. In step S50, the control unit 100 creates an amino acid sequence and/or a base sequence encoding the sequence when at least 3 of the amino acid residues specified in step S47 are changed to basic amino acid residues. Then, in step S51, the control unit 100 transmits the amino acid residues specified in step S47, the electrical characteristic of CDR calculated in step S48, the amino acid sequence of a light chain of a modified antibody created in step S50 and/or the base sequence encoding the amino acid sequence to the output unit 102. In step S49, when the value calculated by the above formula (III) is −2 or less or 2 or more, the electrical characteristic of CDR is determined not to be neutral, and the process proceeds to step S52. In step S52, the control unit 100 transmits the amino acid residues specified in step S47 and the electrical characteristic of CDR calculated in step S48 to the output unit 102.

Hereinafter, the present disclosure will be described in more detail by examples, but the present disclosure is not limited to these examples.

EXAMPLES

Example 1 Preparation of Antibody in which Amino Acid Residue of FR1 or FR3 of Light Chain is Modified Variants of each antibody were prepared by substituting 3 amino acid residues of FR1 or FR3 of an anti-lysozyme antibody with charged amino acid residues.

(1) Obtainment of Gene of Wild-Type Anti-Lysozyme Antibody

Synthesis of anti-lysozyme antibody gene was entrusted to GenScript Japan Inc. to obtain a plasmid DNA containing wild-type anti-lysozyme antibody gene.

(2) Preparation of Variant of Anti-Lysozyme Antibody

[Reagents]
QIAprep Spin Miniprep kit (QIAGEN)
PrimeSTAR (registered trademark) Max DNA Polymerase (Takara Bio Inc.)
Ligation high ver.2 (TOYOBO CO., LTD.)
T4 Polynucleotide Kinase (TOYOBO CO., LTD.)
Dpn I (TOYOBO CO., LTD.)
Competent high DH5α (TOYOBO CO., LTD.)

(2.1) Primer Design and PCR

In order to substitute predetermined 3 amino acid residues of light chain FR1 or FR3 of a wild-type anti-lysozyme antibody with arginine residues, PCR was performed using the plasmid obtained in the above (1) and primers represented by following base sequences. Three numbers in name of each primer indicate positions of amino acid residues substituted with arginine residues in FR of the light chain defined by the Kabat method. Primers of SEQ ID NOs: 1 to 11 were used as forward primers, and primers of SEQ ID NOs: 12 to 22 were used as reverse primers.

[Primer for Preparing Variants]
2, 4, 6 Variant FOR:
(SEQ ID NO: 1)
5'AGAACCAGAAGCCCGGCGACCCTCTCGGTCACCCCCGGC 3'

2, 4, 8 Variant FOR:
(SEQ ID NO: 2)
5' AGAGCAGAGCGACCCTCTCGGTCACCCCCGGC 3'

3, 5, 9 Variant FOR:
(SEQ ID NO: 3)
5' GCCCGCGCACCCTCTCGGTCACCCCCGGC 3'

4, 8, 13 Variant FOR:
(SEQ ID NO: 4)
5' CCCTCTCGAGAACCCCCGGCAACTCGGTGTCGC 3'

5, 9, 22 Variant FOR:
(SEQ ID NO: 5)
5' GGCAACTCGGTGTCGCTCCGCTGCCGCGCCTCGCAGTCG 3'

13, 16, 19 Variant FOR:
(SEQ ID NO: 6)
5 'AACTCGCGATCGCTCTCGTGCCGCGCCTCGCAGTCG 3'

16, 21, 23 Variant FOR:
(SEQ ID NO: 7)
5' GTGTCGCGATCGCGACGCGCCTCGCAGTCGATCGGC 3'

17, 18, 20 Variant FOR:
(SEQ ID NO: 8)
5' CTCTCGTGCCGCGCCTCGCAG 3'

18, 20, 22 Variant FOR:
(SEQ ID NO: 9)
5' CGCTGCCGCGCCTCGCAGTCGATCGGC 3'

19, 21, 23 Variant FOR:
(SEQ ID NO: 10)
5' AGATCGAGACGCGCCTCGCAGTCGATCGGC 3'

63, 65, 67 Variant FOR:
(SEQ ID NO: 11)
5' GGCACCGACTTCACCCTGTCG 3'

2, 4, 6 Variant REV:
(SEQ ID NO: 12)
5' GACTCTATCTCCTCTGGACATTATGACTGAGGC 3'

2, 4, 8 Variant REV:
(SEQ ID NO: 13)
5' GGGTTCTGACTCTATCTCCTCTGGACATTATGACTGAGGC 3'

3, 5, 9 Variant REV:
(SEQ ID NO: 14)
5' TCTGGCGCAGGCGGATATCTCCTCTGGACATTATG 3'

4, 8, 13 Variant REV:
(SEQ ID NO: 15)
5' TCGCTCTGCTCTGGGTTCTGACGATATCTCCTCTGGACATTATG 3'

5, 9, 22 Variant REV:
(SEQ ID NO: 16)
5' GGGGGTGACCGAGAGGGTGCGCGGGCTCTGGCGCAGGACGATATCTCCTCTGG 3'

13, 16, 19 Variant REV:
(SEQ ID NO: 17)
5' TCGGGGGGTTCGCGAGAGGGTCGCCGGGCTCTGGG 3'

16, 21, 23 Variant REV:
(SEQ ID NO: 18)
5' CGAGTTTCGGGGGGTGACCGAGAGGGTCGC 3'

17, 18, 20 Variant REV:
(SEQ ID NO: 19)
5' GCGCACGCGGCGGCCGGGGGTGACCGAGAGGG 3'

18, 20, 22 Variant REV:
(SEQ ID NO: 20)
5' GAGGCGCACGCGGTTGCCGGGGGTGACCGAGAGGG 3'

19, 21, 23 Variant REV:
(SEQ ID NO: 21)
5' CGATCTCGAGTTGCCGGGGGTGACCGAGAGGG 3'

63, 65, 67 Variant REV:
(SEQ ID NO: 22)
5' TCTGCCTCTGCCTCTGAAGCGCGACGGGATCCCCG 3'

Using the plasmid obtained in the above (1) as a template, a PCR reaction solution with the following composition was prepared.

PCR Reaction Solution

| | |
|---|---|
| PrimeSTAR (registered trademark) Max DNA Polymerase | 12.5 μL |
| Forward primer (10 μM) | 1 μL |
| Reverse primer (10 μM) | 1 μL |
| Template plasmid (3 ng/μL) | 1 μL |
| Purified water | 9.5 μL |
| Total | 25 μL |

The prepared PCR reaction solution was subjected to a PCR reaction under the following reaction conditions.

Reaction Conditions 30 cycles at 98° C. for 10 seconds, 98° C. for 10 seconds, 54° C. for 10 seconds and 72° C. for 45 seconds, and at 72° C. for 3 minutes.

The obtained PCR product was fragmented by adding 1 μL of DpnI (10 U/μL) to the PCR product (25 μL). Using the DpnI-treated PCR product, a ligation reaction solution with the following composition was prepared. The reaction solution was incubated at 16° C. for 1 hour to perform a ligation reaction.

Ligation Reaction Liquid

| | |
|---|---|
| DpnI-treated PCR product | 2 μL |
| Ligation high ver.2 | 5 μL |
| T4 Polynucleotide kinase | 1 μL |
| Purified water | 7 μL |
| Total | 15 μL |

(2.2) Transformation, Plasmid Extraction and Sequence Confirmation

The solution (3 μL) after the ligation reaction was added to DH5α (30 μL), and the mixture was allowed to stand on ice for 30 minutes. Thereafter, the mixture was heat shocked by heating at 42° C. for 45 seconds. The mixture was again allowed to stand on ice for 2 minutes, then the whole amount was applied to an ampicillin-containing LB plate. The plate was incubated at 37° C. for 16 hours to obtain *E. coli* transformants. Single colonies on the plate were placed in the ampicillin-containing LB liquid medium, and the medium was shake-cultured (250 rpm) at 37° C. for 16 hours. Plasmids were extracted from the obtained *E. coli* using the QIAprep Spin Miniprep kit. The base sequence of each obtained plasmid was confirmed using pcDNA 3.4 vector primer. Hereinafter, these plasmids were used as plasmids for expressing mammalian cells.

(3) Expression in Mammalian Cells

Reagents

Expi293 (trademark) Cells (Invitrogen)
Expi293 (trademark) Expression medium (Invitrogen)
ExpiFectamine (trademark) 293 transfection kit (Invitrogen)

(3.1) Transfection

Expi293 Cells were proliferated by shaking culture (150 rpm) at 37° C. in a 5% $CO_2$ atmosphere. 30 mL of cell culture ($3.0 \times 10^6$ cells/mL) was prepared according to the number of samples. A DNA solution with the following composition was prepared using a plasmid encoding each variant and a plasmid encoding a wild-type antibody. The DNA solution was allowed to stand for 5 minutes.

DNA Solution

| | |
|---|---|
| Light chain plasmid solution | Amount (μL) corresponding to 15 μg |
| Heavy chain plasmid solution | Amount (μL) corresponding to 15 μg |
| Opti-MEM (trademark) | Appropriate amount (mL) |
| Total | 1.5 mL |

A transfection reagent with the following composition was prepared. The transfection reagent was allowed to stand for 5 minutes.

| | |
|---|---|
| ExpiFectamine reagent | 80 μL |
| Light chain plasmid solution | 1420 μL |
| Total | 1.5 mL |

The prepared DNA solution and the transfection reagent were mixed. The mixture was allowed to stand for 20 minutes. The resulting mixture (3 mL) was added to the cell culture (30 mL). The mixture was shake-cultured (150 rpm) at 37° C. for 20 hours in a 5% $CO_2$ atmosphere. After 20 hours, 150 μL and 1.5 mL of ExpiFectamine (trademark) transfection enhancers 1 and 2 were added to each culture, respectively. Each mixture was shake-cultured (150 rpm) at 37° C. for 6 days in a 5% $CO_2$ atmosphere.

(3.2) Recovery and Purification of Antibody

Each cell culture was centrifuged at 3000 rpm for 5 minutes, and the culture supernatant was recovered. The culture supernatant contains each antibody secreted from transfected Expi293 (trademark) cells. The obtained culture supernatant was again centrifuged at 15000×G for 10 minutes, and the supernatant was recovered. To the obtained supernatant (30 mL) was added 100 μL of antibody purification carrier Ni Sepharose High Performance (GE Healthcare), and the mixture was reacted at room temperature for 2 hours. The carrier was recovered to remove the supernatant, and TBS (1 mL) was added to wash the carrier. To the carrier was added 1000 μL of TBS containing 100 mM imidazole to elute the antibody captured on the carrier. This elution operation was performed a total of 3 times to obtain an antibody solution.

(4) Measurement of Affinity

The affinity of the prepared variants was measured using Biacore (registered trademark) T200 (GE Healthcare). Chicken egg white-derived lysozyme (Sigma-Aldrich) was used as an antigen for the anti-lysozyme antibody. Antigen was immobilized (immobilization: 50 RU) to a sensor chip for Biacore (registered trademark) Series S Sensor Chip CM5 (GE Healthcare). The antibody solution was diluted to prepare antibody solutions of 30 nM, 15 nM, 7.5 nM, 3.75 nM and 1875 nM. The antibody solutions at each concentration were delivered to Biacore (registered trademark) T200 (GE Healthcare) (association time of 120 seconds and dissociation time of 1800 seconds). Measurement data was analyzed using Biacore (registered trademark) Evaluation software, and the data on the affinity of each antibody was obtained. Kd values of each antibody are shown in Table 2.

TABLE 2

| Anti-lysozyme antibody | $K_d$ (M) |
|---|---|
| Wild-type | 1.31E−10 |
| 63, 65, 67 Variant | 9.20E−11 |
| 18, 20, 22 Variant | 6.52E−11 |
| 3, 5, 9 Variant | 7.23E−11 |
| 17, 18, 20 Variant | 1.05E−10 |
| 5, 9, 22 Variant | 6.90E−11 |

(5) Result

As shown in Table 2, Kd values of 63, 65, 67 variant in which FR3 of a light chain was modified, 18, 20, 22 variant in which FR1 of a light chain was modified, 3, 5, 9 variant, 17, 18, 20 variant, 18, 20, 22 variant and 5, 9, 22 variant were lower than Kd value of the wild-type anti-lysozyme antibody. Therefore, the variants shown in Table 2 had improved affinity for an antigen as compared to the wild-type by changing 3 amino acid residues of FR3 or FR1 to basic amino acid residues.

Figure 9:
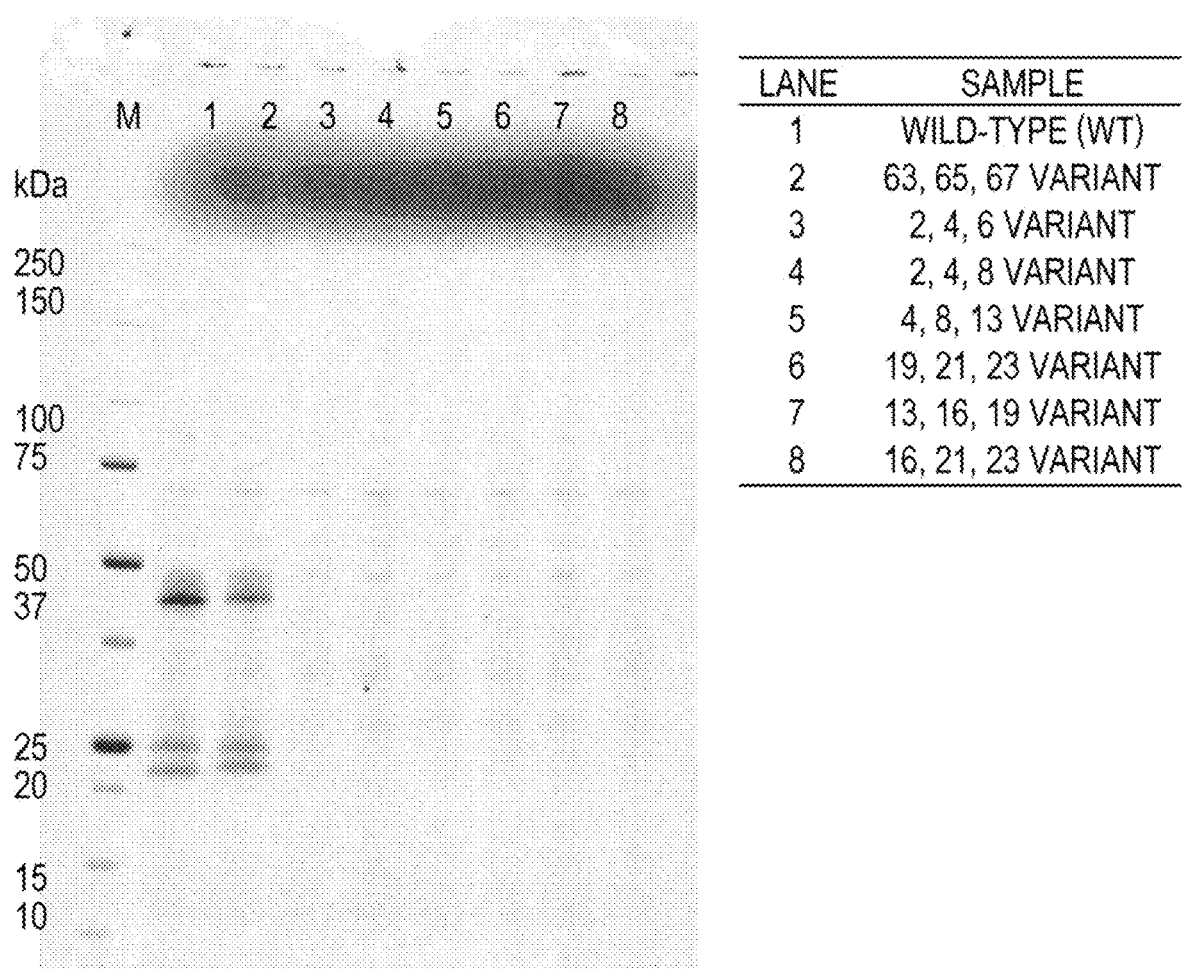
FIG. 9 is a photograph of a gel in which an antibody eluate was separated by SDS-PAGE and stained with Coomassie Brilliant Blue (CBB).

On the other hand, for the variants not shown in Table 2, antibody expression was not observed in the first place. Expression was confirmed by analyzing the eluate obtained in the above (3.2) by SDS-PAGE and CBB staining. The results are shown in FIG. 9. As can be seen from FIG. 9, heavy chain and light chain bands of the antibody were observed in lanes 1 and 2. Therefore, expression of wild-type antibody and 63, 65, 67 variant was observed. However, no antibody band was observed in lanes 3 to 8, so that expression of 2, 4, 6 variant, 2, 4, 8 variant, 4, 8, 13 variant, 19, 21, 23 variant, 13, 16, 19 variant and 16, 21, 23 variant were not observed.

Example 2 Characteristics of Antibody with Improved Affinity for Antigen

In order to find features common to the variants of Example 1 with improved affinity for an antigen, the present inventors calculated amino acid frequencies at each position of FR1 and FR3 of the light chains. The present inventors considered that a side chain of the amino acid residue facing the surface of the antibody molecule is involved in the improvement in affinity for an antigen, and calculated ratios of solvent-exposed surface areas of each amino acid residue of FR1 and FR3 of the light chains.

(1) Amino Acid Frequency

Amino acid sequences of light chains of about 30,000 mouse antibodies were downloaded as reference antibodies from abYsis, a public database that provides amino acid sequences of antibodies. The obtained amino acid sequences of light chains of reference antibodies were aligned so that the numbers of the amino acid residues in FR of the light chains assigned by Kabat method matched. Amino acid frequencies at each position of FR1 and FR3 of the obtained light chains of reference antibodies were obtained. Sequence alignment and amino acid frequencies were obtained by abYsis. It was found that appearance frequencies of R, S, T, V, D and E tended to be high at positions corresponding to the amino acid residues modified by the variants of Example 1 with improved affinity for an antigen. Therefore, total value of these amino acid frequencies was calculated at each position of FR1 and FR3 of the light chains. The total value of amino acid frequencies was calculated by the above formula (I). Here, the obtained numbers by the Kabat method assigned to FRs of light chains of reference antibodies were the same for FR of a light chain of a wild-type anti-lysozyme antibody. Therefore, the total value of amino acid frequencies obtained from the amino acid sequences of light chains of reference antibodies was used as a value for the amino acid sequence of a light chain of a wild-type anti-lysozyme antibody.

(2) Ratio of Solvent-Exposed Surface Area

An amino acid sequence of a light chain of a wild-type anti-lysozyme antibody was retrieved from PDB, a public database that provides three-dimensional structure data of proteins, and three-dimensional structure data of a light chain of the antibody was downloaded. Using the obtained three-dimensional structure data, ratios of solvent-exposed surface areas of each amino acid residue of FR1 and FR3 of a light chain of a wild-type anti-lysozyme antibody were obtained by Discovery Studio Client v17.2.0.16349. In Discovery Studio Client v17.2.0.16349, the ratios of solvent-exposed surface area were calculated by the above formula (II).

(3) Result

Table 3 and Tables 4A and 4B show the amino acid frequencies of R, S, T, V, D and E at each position of FR1 and FR3 of a light chain of a wild-type anti-lysozyme antibody and their total values, and the ratios of solvent-exposed surface areas of each amino acid residue.

TABLE 3

| Position of FR1 of light chain | L1 | L2 | L3 | L4 | L5 | L6 | L7 | L8 | L9 | L10 | L11 | L12 |
|---|---|---|---|---|---|---|---|---|---|---|---|---|
| R | 0.2 | 0.1 | 0.6 | 0.0 | 0.1 | 0.1 | 0.1 | 1.0 | 0.1 | 0.0 | 0.1 | 0.1 |
| S | 7.3 | 16.6 | 1.8 | 0.1 | 4.6 | 3.1 | 49.9 | 6.0 | 55.9 | 58.6 | 0.4 | 79.1 |
| T | 0.2 | 1.6 | 2.4 | 0.4 | 88.5 | 1.4 | 11.7 | 1.7 | 1.1 | 23.5 | 0.7 | 3.4 |
| V | 0.2 | 9.1 | 53.4 | 7.5 | 0.1 | 0.0 | 0.2 | 0.2 | 2.1 | 1.3 | 29.0 | 0.3 |
| D | 37.4 | 0.3 | 1.0 | 0.0 | 0.3 | 0.2 | 1.5 | 0.1 | 3.4 | 0.0 | 0.0 | 0.0 |
| E | 17.7 | 0.1 | 8.6 | 0.1 | 0.1 | 0.1 | 2.8 | 0.2 | 0.6 | 0.0 | 0.2 | 0.3 |
| Total value of amino acid frequencies (%) | 62.9 | 27.7 | 67.8 | 8.2 | 93.8 | 4.9 | 66.2 | 9.1 | 63.2 | 83.5 | 30.3 | 83.1 |
| Ratio of solvent-exposed surface area (%) | 69.0 | 7.1 | 88.1 | 0.0 | 84.8 | 0.0 | 100.0 | 54.8 | 111.5 | 74.0 | 26.8 | 57.7 |

| Position of FR1 of light chain | L13 | L14 | L15 | L16 | L17 | L18 | L19 | L20 | L21 | L22 | L23 |
|---|---|---|---|---|---|---|---|---|---|---|---|
| R | 0.2 | 0.1 | 0.1 | 0.7 | 0.3 | 44.7 | 0.0 | 5.7 | 0.0 | 0.5 | 0.1 |
| S | 1.1 | 69.3 | 0.5 | 0.2 | 0.9 | 10.7 | 0.1 | 16.0 | 0.0 | 47.5 | 0.1 |

TABLE 3-continued

| | | | | | | | | | | | |
|---|---|---|---|---|---|---|---|---|---|---|---|
| T | 3.5 | 11.8 | 0.6 | 0.0 | 0.4 | 24.3 | 0.1 | 70.6 | 0.1 | 42.9 | 0.0 |
| V | 31.2 | 0.3 | 21.9 | 0.1 | 0..0 | 0.1 | 61.1 | 0.2 | 1.4 | 0.0 | 0.0 |
| D | 0.0 | 0.1 | 0.0 | 0.1 | 25.5 | 0.0 | 0.0 | 0.0 | 0.0 | 0.1 | 0.0 |
| E | 1.5 | 0.0 | 0.1 | 0.3 | 31.0 | 0.2 | 0.0 | 1.0 | 0.0 | 0.2 | 0.0 |
| Total value of amino acid frequencies (%) | 37.5 | 81.6 | 23.2 | 1.4 | 58.1 | 80.0 | 61.4 | 93.5 | 1.5 | 91.1 | 0.2 |
| Ratio of solvent-exposed surface area (%) | 10.9 | 67.7 | 30.6 | 81.7 | 85.1 | 79.9 | 4.6 | 81.5 | 1.5 | 25.7 | 0.0 |

TABLE 4A

| Position of FR3 of light chain | L57 | L58 | L59 | L60 | L61 | L62 | L63 | L64 | L65 | L66 | L67 | L68 |
|---|---|---|---|---|---|---|---|---|---|---|---|---|
| R | 0.22 | 0.00 | 0.04 | 0.04 | 98.50 | 0.00 | 0.95 | 0.03 | 1.01 | 3.68 | 0.05 | 0.99 |
| S | 0.10 | 0.07 | 6.72 | 27.74 | 0.13 | 0.12 | 88.20 | 0.73 | 95.85 | 3.85 | 93.33 | 2.23 |
| T | 0.03 | 2.07 | 0.33 | 0.64 | 0.17 | 0.01 | 5.67 | 0.02 | 0.92 | 1.13 | 0.25 | 0.18 |
| V | 0.06 | 66.28 | 0.00 | 1.06 | 0.00 | 0.25 | 0.77 | 0.23 | 0.03 | 0.87 | 0.03 | 0.16 |
| D | 2.09 | 0.07 | 0.00 | 43.09 | 0.00 | 0.02 | 0.01 | 0.19 | 0.06 | 0.05 | 0.12 | 0.87 |
| E | 0.41 | 0.03 | 0.01 | 7.11 | 0.00 | 0.00 | 0.02 | 0.02 | 0.04 | 0.35 | 0.04 | 0.80 |
| Total value of amino acid frequencies (%) | 2.89 | 68.52 | 7.10 | 79.67 | 98.81 | 0.39 | 95.62 | 1.20 | 97.91 | 9.93 | 93.82 | 5.22 |
| Ratio of solvent-exposed surface area (%) | 123.56 | 6.65 | 25.77 | 132.72 | 13.71 | 0.34 | 84.95 | 2.09 | 93.83 | 54.45 | 85.39 | 46.07 |

| Position of FR3 of light chain | L69 | L70 | L71 | L72 | L73 | L74 | L75 | L76 | L77 | L78 | L79 | L80 |
|---|---|---|---|---|---|---|---|---|---|---|---|---|
| R | 0.69 | 0.22 | 1.33 | 0.05 | 0.01 | 0.96 | 0.01 | 0.78 | 17.70 | 0.09 | 2.96 | 1.01 |
| S | 5.49 | 16.37 | 0.58 | 26.20 | 0.09 | 2.58 | 0.06 | 73.92 | 35.17 | 0.06 | 0.07 | 12.11 |
| T | 68.95 | 18.75 | 0.14 | 65.26 | 0.15 | 74.45 | 0.17 | 14.80 | 1.31 | 2.22 | 0.04 | 8.53 |
| V | 0.05 | 0.44 | 1.34 | 0.39 | 0.06 | 0.35 | 1.72 | 0.03 | 0.04 | 28.04 | 0.25 | 1.55 |
| D | 2.22 | 44.95 | 0.17 | 0.03 | 0.00 | 0.26 | 0.00 | 0.59 | 1.39 | 0.01 | 0.47 | 0.13 |
| E | 0.10 | 8.77 | 0.01 | 0.00 | 0.01 | 0.19 | 0.00 | 0.29 | 0.26 | 0.01 | 33.22 | 1.73 |
| Total value of amino acid frequencies (%) | 77.50 | 89.49 | 3.57 | 91.94 | 0.32 | 78.79 | 1.96 | 90.41 | 55.86 | 30.44 | 37.00 | 25.05 |
| Ratio of solvent-exposed surface area (%) | 69.13 | 63.96 | 0.00 | 53.09 | 0.00 | 58.10 | 0.00 | 93.56 | 82.29 | 0.00 | 61.80 | 44.13 |

TABLE 4B

| Position of FR3 of light chain | L81 | L82 | L83 | L84 | L85 | L86 | L87 | L88 |
|---|---|---|---|---|---|---|---|---|
| R | 0.03 | 0.01 | 0.00 | 0.01 | 0.05 | 0.00 | 0.01 | 0.09 |
| S | 0.04 | 0.00 | 1.00 | 0.65 | 1.41 | 0.02 | 0.62 | 0.05 |
| T | 0.17 | 0.01 | 0.75 | 0.44 | 27.76 | 0.00 | 0.01 | 0.00 |
| V | 0.25 | 0.06 | 11.70 | 0.66 | 27.58 | 0.01 | 0.05 | 0.02 |
| D | 8.60 | 99.26 | 0.74 | 0.04 | 32.55 | 0.00 | 0.00 | 0.00 |
| E | 81.18 | 0.19 | 34.30 | 0.01 | 1.68 | 0.00 | 0.00 | 0.00 |
| Total value of amino acid frequencies (%) | 90.27 | 99.53 | 48.49 | 1.81 | 91.03 | 0.03 | 0.69 | 0.16 |
| Ratio of solvent-exposed surface area (%) | 77.62 | 1.49 | 7.43 | 8.38 | 15.55 | 0.00 | 1.01 | 0.00 |

From these tables, as a feature common to the variants of Example 1 with improved affinity for an antigen, it was found that 3 of the amino acid residues satisfying both following conditions (a) and (b) in the amino acid sequence of FR of a light chain of an antibody were changed to charged amino acid residues. It was found that the amino acid residues modified by a variant whose expression could not be confirmed in Example 1 did not satisfy following conditions (a) and/or (b).

(a) In the amino acid sequence of FR of a light chain of an antibody, present at positions where total value of amino acid frequencies of arginine, serine, threonine, valine, aspartic acid and glutamic acid is 35% or more.

(b) In the amino acid sequence of FR of a light chain of an antibody, has a ratio of solvent-exposed surface area of 20% or more.

Example 3 Preparation of Antibody in which Amino Acid Residue of FR3 of Light Chain is Modified Whether the affinity of the antibody for an antigen could be improved by substituting 3 of the amino acid residues satisfying both the above conditions (a) and (b) found in Example 2 with charged amino acid residues was verified. Specifically, a variant of anti-lysozyme antibody different from the variants prepared in Example 1 were prepared, and their affinity for an antigen was measured.

(1) Preparation of Variant of Anti-Lysozyme Antibody

Three amino acid residues to be modified in light chain FR3 of a wild-type anti-lysozyme antibody were selected from Tables 4A and 4B. In order to substitute the 3 selected predetermined amino acid residues with arginine residues, PCR was performed in the same manner as in Example 1 using primers represented by following base sequences. Primers of SEQ ID NOs: 23 to 28 were used as forward primers, and primers of SEQ ID NOs: 29 to 34 were used as reverse primers.

```
[Primer for Preparing Variants]
60, 63, 65 Variant FOR:
                                       (SEQ ID NO: 23)
5' GAGGCTCGGGCACCGACTTCACCCTGTC 3'

60, 76, 77 Variant FOR:
                                       (SEQ ID NO: 24)
5' TCGGGCACCGACTTCACCCTGTCGATCAGAAGAGTCGAGACGGAGGC
3'

65, 67, 70 Variant FOR:
                                       (SEQ ID NO: 25)
5' CCAGATTCACCCTGTCGATCAACAGCGTCGAG 3'

67, 70, 72 Variant FOR:
                                       (SEQ ID NO: 26)
5' CCAGATTCAGACTGTCGATCAACAGCGTCGAGAC 3'

74, 76, 77 Variant FOR:
                                       (SEQ ID NO: 27)
5' AGTCGAGACGGAGGACTTCGG 3'

77, 79, 81 Variant FOR:
                                       (SEQ ID NO: 28)
5' AGAACGAGAGACTTCGGCATGTACTTCTGC 3'

60, 63,65 Variant REV:
                                       (SEQ ID NO: 29)
5' TGCCTCTGAAGCGTCTCGGGATCCCCGAGATC 3'

60, 76, 77 Variant REV:
                                       (SEQ ID NO: 30)
5' GCCCGAGCCGCTGAAGCGTCTCGGGATCCCCGAGATC 3'

65, 67, 70 Variant REV:
                                       (SEQ ID NO: 31)
5' TGCCTCTGCCTCTGCCGCTGAAGC 3'

67, 70, 72 Variant REV:
                                       (SEQ ID NO: 32)
5' TGCCTCTGCCCGAGCCGCTGAAG 3'

74, 76, 77 Variant REV:
                                       (SEQ ID NO: 33)
5' CTTCTGATTCTCAGGGTGAAGTCG 3'

77, 79, 81 Variant REV:
                                       (SEQ ID NO: 34)
5' GACTCTGTTGATCGACAGGGTGAAGTCG 3'
```

Using the obtained PCR product, plasmids containing a gene encoding a light chain of variant and a plasmid containing a gene encoding a wild-type heavy chain were obtained in the same manner as in Example 1. Using these plasmids, each antibody was expressed in Expi293 (trademark) cells, and the resulting culture supernatant was purified in the same manner as in Example 1 to obtain a solution of variant of anti-lysozyme antibody.

(2) Measurement of Affinity

The affinity of the prepared variants was measured using Biacore (registered trademark) T200 (GE Healthcare) in the same manner as in Example 1. The results are shown in Table 5.

TABLE 5

| Anti-lysozyme antibody | $K_d$ (M) |
|---|---|
| Wild-type | 1.3E-10 |
| 60, 63, 65 Variant | 6.6E-11 |
| 67, 70, 72 Variant | 1.4E-11 |
| 74, 76, 77 Variant | 5.6E-11 |
| 77, 79, 81 Variant | 1.0E-10 |
| 65, 67, 70 Variant | 2.0E-11 |
| 60, 76, 77 Variant | 9.7E-11 |

As shown in Table 5, Kd values of all the variants were lower than the Kd value of the wild-type anti-lysozyme antibody. Therefore, it was suggested that the affinity of the antibody for an antigen can be improved by substituting 3 of the amino acid residues satisfying both the above conditions (a) and (b) found in Example 2 with arginine residues.

Example 4 Preparation of Antibody in which Amino Acid Residue of FR1 or FR3 of Light Chain is Modified (2)

As unmodified antibodies, a mouse anti-lysozyme antibody of clone (Hy-HEL5) different from the anti-lysozyme antibody of Example 1, a mouse anti-thyroid stimulating hormone (TSH) antibody, and a humanized anti-HER2 antibody (trastuzumab) were used. In FR1 or FR3 of light chains of these antibodies, whether the affinity of the antibody for an antigen can be improved by substituting 3 of the amino acid residues satisfying both the above conditions (a) and (b) with charged amino acid residues was verified.

(1) Preparation of Variants (1.1) Obtainment of Gene Encoding Light Chain of Variant of Anti-Lysozyme Antibody (Hy-HEL5)

From Table 3, 3rd, 5th and 9th amino acid residues of light chain FR1 were selected as the amino acid residues satisfying both the above conditions (a) and (b). In order to substitute these amino acid residues with histidine residues, PCR was performed in the same manner as in Example 1 using primers represented by following base sequences. A primer of SEQ ID NO: 46 was used as a forward primer, and a primer of SEQ ID NO: 47 was used as a reverse primer.

```
3, 5, 9 Variant (His) FOR:
                                       (SEQ ID NO: 46)
5' CATCTGCACCAATCACCGCACATTATGTCCGCATCTC 3'

3, 5, 9 Variant (His) REV:
                                       (SEQ ID NO: 47)
5' TATGTCCCCTCTGCTCATAATCACAGAGGCACTG 3'
```

(1.2) Obtainment of Gene Encoding Light Chain of Variant of Anti-TSH Antibody

The total values of amino acid frequencies shown in Table 3 were used as total values of amino acid frequencies of R, S, T, V, D and E at each position of an amino acid sequence of light chain FR of a wild-type anti-TSH antibody. Ratios of solvent-exposed surface area of each amino acid residue of the light chain FR of the anti-TSH antibody were obtained based on three-dimensional structure data of a light chain of a wild-type anti-TSH antibody downloaded from the database PDB in the same manner as in Example 2. 18th, 20th and 22nd Amino acid residues of the light chain FR1 were selected as the amino acid residues satisfying both the above conditions (a) and (b). In order to substitute these amino acid residues with lysine residues, PCR was performed in the same manner as in Example 1 using primers represented by following base sequences. A primer of SEQ ID NO: 48 was used as a forward primer, and a primer of SEQ ID NO: 49 was used as a reverse primer.

```
18, 20, 22 Variant (Lys) FOR:
                                      (SEQ ID NO: 48)
5' AAGGCCAAGATTAAGTGCAGATCTAATCAGAGCGTTG 3'

18, 20, 22 Variant (Lys) REV:
                                      (SEQ ID NO: 49)
5' ATCTCCAAGACTGACAGGCAGGGAGAGTG 3'
```

(1.3) Obtainment of Gene Encoding Light Chain of Variant of Humanized Anti-HER2 Antibody Amino acid sequences of light chains of about 30,000 human antibodies were downloaded as reference antibodies from database abYsis. In the same manner as in Example 2, the obtained amino acid sequences of light chains of reference antibodies were aligned, and total value of amino acid frequencies of R, S, T, V, D and E at each position of the amino acid sequence of FR was calculated. The ratio of solvent-exposed surface area of each amino acid residue of the light chain FR of the anti-HER2 antibody was obtained based on three-dimensional structure data of a light chain of a humanized anti-HER2 antibody downloaded from the database PDB in the same manner as in Example 2. 76th, 77th and 81st Amino acid residues of the light chain FR3 were selected. In order to substitute these amino acid residues with arginine residues, PCR was performed in the same manner as in Example 1 using primers represented by following base sequences. A primer of SEQ ID NO: 50 was used as a forward primer, and a primer of SEQ ID NO: 51 was used as a reverse primer.

```
76, 77, 81 Variant (Arg) FOR:
                                      (SEQ ID NO: 50)
5' CAGCCGAGAGACTTCGCCACGTATTACTG 3'

76, 77, 81 Variant (Arg) REV:
                                      (SEQ ID NO: 51)
5' CAGTCTTCTGATCGTCAGGGTAAAATCGGTAC 3'
```

(1.4) Obtainment of Variants of Each Antibody

Using the obtained PCR product, plasmids containing a gene encoding a light chain of variant of each antibody and a plasmid containing a gene encoding a wild-type heavy chain of each antibody were obtained in the same manner as in Example 1. Using these plasmids, each antibody was expressed in Expi293 (trademark) cells, and the resulting culture supernatant was purified in the same manner as in Example 1 to obtain a solution of variant of each antibody. An amino acid sequence of a light chain of 76, 77, 81 variant (Arg) of the humanized anti-HER2 antibody is shown in SEQ ID NO: 52.

(2) Measurement of Affinity

The affinity of the prepared variants was measured using Biacore (registered trademark) T200 (GE Healthcare) in the same manner as in Example 1. In the measurement, TSH protein (R&D Systems, Inc.) was used as an antigen of the anti-TSH antibody, and HER2 protein (R&D Systems, Inc., Catalog No. 1129-ER) was used as an antigen of the anti-HER2 antibody. The results are shown in Table 6. In the table, "Ratio" is a ratio of Kd value of variant type when Kd value of wild-type is 1.

TABLE 6

|  | $K_d$ (M) | Ratio |
|---|---|---|
| Anti-lysozyme antibody | | |
| Wild-type | 1.77E−10 | 1.00 |
| 3, 5, 9 Variant (His) | 1.21E−10 | 1.46 |
| Anti-TSH antibody | | |
| Wild-type | 1.18E−09 | 1.00 |
| 18, 20, 22 Variant (Lys) | 4.64E−10 | 2.55 |
| Anti-HER2 antibody | | |
| Wild-type | 5.94E−11 | 1.00 |
| 76, 77, 81 Variant (Arg) | 2.19E−11 | 2.71 |

As shown in Table 6, Kd values of all the variants were lower than Kd values of the wild-type antibodies. Therefore, even for an antibody different from the anti-lysozyme antibody of Example 1, it was suggested that the affinity of the antibody for an antigen can be improved by modifying 3 of the amino acid residues satisfying both the above conditions (a) and (b).

---

The invention claimed is:

1. A method for improving affinity of an antibody or an antibody fragment for an antigen, comprising improving affinity of the antibody or the antibody fragment by changing 18th, 20th and 22nd amino acid residues defined by Kabat method of a light chain of the antibody or the antibody fragment to charged amino acid residues.

2. The method according to claim 1, wherein the charged amino acid residue is a basic amino acid residue.

3. The method according to claim 2, wherein the basic amino acid residue is an arginine residue or a lysine residue.

4. The method according to claim 1, wherein the antibody fragment is a Fab fragment, a F (ab')2 fragment, a Fab' fragment, an Fv fragment, a dAb fragment, an scFv, or an rIgG.

5. A method for producing an antibody or an antibody fragment with improved affinity, comprising:
changing 18th, 20th and 22nd amino acid residues defined by Kabat method of a light chain of the antibody or the antibody fragment to charged amino acid residues; and
recovering the antibody obtained in the changing.

6. The method according to claim 5, wherein the charged amino acid residue is a basic amino acid residue.

7. The method according to claim 6, wherein the basic amino acid residue is an arginine residue or a lysine residue.

8. The method according to claim 5, wherein the antibody fragment is a Fab fragment, a F (ab')2 fragment, a Fab' fragment, an Fv fragment, a dAb fragment, an scFv, or an rIgG.

9. A modified antibody or a modified antibody fragment with improved affinity for an antigen, wherein 18th, 20th and 22nd amino acid residues defined by Kabat method of a light chain are changed to charged amino acid residues.

10. The modified antibody or the modified antibody fragment according to claim 9, wherein the charged amino acid residue is a basic amino acid residue.

11. The modified antibody or the modified antibody fragment according to claim 10, wherein the basic amino acid residue is an arginine residue or a lysine residue.

12. The modified antibody or the modified antibody fragment according to claim 9, wherein the antibody fragment is a Fab fragment, a F (ab')2 fragment, a Fab' fragment, an Fv fragment, a dAb fragment, an scFv, or an rIgG.

* * * * *